United States Patent
Wei et al.

(10) Patent No.: US 10,597,634 B2
(45) Date of Patent: Mar. 24, 2020

(54) DEVICE AND USE THEREOF IN CELL EXPERIMENTS IN VITRO

(71) Applicant: Peking University School And Hospital Of Stomatology, Beijing (CN)

(72) Inventors: Shicheng Wei, Beijing (CN); Ping Zhou, Beijing (CN); Xiaohong Zhang, Beijing (CN); Yongliang Li, Beijing (CN); Mengke Wang, Beijing (CN)

(73) Assignee: Peking University School and Hospital of Stomatology, Beijing (CN)

( * ) Notice: Subject to any disclaimer, the term of this patent is extended or adjusted under 35 U.S.C. 154(b) by 0 days.

(21) Appl. No.: 15/540,700

(22) PCT Filed: Dec. 9, 2015

(86) PCT No.: PCT/CN2015/096857
§ 371 (c)(1),
(2) Date: Jun. 29, 2017

(87) PCT Pub. No.: WO2016/107387
PCT Pub. Date: Jul. 7, 2016

(65) Prior Publication Data
US 2018/0142205 A1    May 24, 2018

(30) Foreign Application Priority Data
Dec. 31, 2014  (CN) .................. 2014 1 0850755.0

(51) Int. Cl.
*A61K 38/10* (2006.01)
*C12N 5/0735* (2010.01)
*C12M 1/00* (2006.01)
*C12N 5/16* (2006.01)

(52) U.S. Cl.
CPC .......... *C12N 5/0606* (2013.01); *C12M 23/20* (2013.01); *C12N 5/16* (2013.01); *C12N 2500/38* (2013.01); *C12N 2501/115* (2013.01); *C12N 2501/13* (2013.01); *C12N 2501/155* (2013.01); *C12N 2501/998* (2013.01)

(58) Field of Classification Search
None
See application file for complete search history.

(56) References Cited

U.S. PATENT DOCUMENTS

| 9,133,246 B2* | 9/2015 | Chung ................ A61L 27/24 |
| 2005/0147645 A1* | 7/2005 | Budny ................ A61L 27/02 424/423 |
| 2013/0164787 A1* | 6/2013 | Agulnick et al. ....... C12P 21/00 435/71.1 |
| 2015/0010999 A1* | 1/2015 | Caracci ................ C12N 5/0037 435/366 |

FOREIGN PATENT DOCUMENTS

WO    2013-116432 A1    8/2013

OTHER PUBLICATIONS

Shi et al., Surface Functionalization of Titanium with Carboxymethyl Chitosan and Immobilized Bone Morphogenetic Protein-2 for Enhanced Osseointegration, Biomacromolecules, vol. 10, No. 6, pp. 1603-1611.*
Melkoumian, et al., "Synthetic Peptide-Acrylate Surfaces for Long-Term Self-Renewal and Cardiomyocyte Differentiation of Human Embryonic Stem Cells," Nature Biotechnology, vol. 28, No. 6, Jun. 2010, 606-612.
Shi, et al. "Surface Functionalization of Titanium with Carboxymethyl Chitosan and Immobilized Bone Morphogenetic Protein-2 for Enhanced Osseointegration," Biomacromolecules, 2009, 10 (6), pp. 1603-1611.
Sun, et al., "Construction of stem cell culture microenvironment on culture dish surface by covalently grafted biomolecules and evaluation on its adhesion function," Proceedings of the 8th National Symposium on Dental Materials, Aug. 31, 2013.
Villa-Diaz, et al., "Synthetic Polymer Coatings for Long-term Growth of human Embryonic Stem Cells," Nature Biotechnology, vol. 28, No. 6, Jun. 2010, 581-583.
Wang, Mengke, et al. "In vitro culture and directed osteogenic differentiation of human pluripotent stem cells on peptides-decorated two-dimensional microenvironment." ACS applied materials & interfaces 7, No. 8 (2015): 4560-4572.
Xu et al, "Feeder-Free Growth of Undifferentiated Human Embryonic Stem Cells," Nature Biotechnology, vol. 19, Oct. 2001, 971-974.
Yang et al., "Human Cardiovascular Progenitor Cells Develop from a KDR+Embryonic-Stem-Cell-Derived Population," Nature, vol. 453, May 22, 2008, 524-529.

* cited by examiner

*Primary Examiner* — Maury A Audet
(74) *Attorney, Agent, or Firm* — Kilpatrick Townsend & Stockton LLP

(57) ABSTRACT

The invention provides a device and the use thereof in a cell experiment in vitro. This device has a polydopamine layer-carboxymethyl chitosan layer-peptide layer structure, which is capable of regulating behaviors of human pluripotent stem cells and is useful in cell culture or a cell experiment in vitro.

11 Claims, 10 Drawing Sheets
Specification includes a Sequence Listing.

SEQUENCE LISTING

<160> NUMBER OF SEQ ID NOS: 32

<210> SEQ ID NO 1
<211> LENGTH: 15
<212> TYPE: PRT
<213> ORGANISM: Artificial Sequence
<220> FEATURE:
<223> OTHER INFORMATION: Synthetic construct

<400> SEQUENCE: 1

Lys Gly Gly Pro Gln Val Thr Arg Gly Asp Val Phe Thr Met Pro
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic construct

<400> SEQUENCE: 2

Lys Gly Gly Pro Gln Val Thr Arg Gly Asp Thr Tyr Arg Ala Tyr
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic construct

<400> SEQUENCE: 3

Lys Gly Gly Asn Gly Glu Pro Arg Gly Asp Thr Tyr Arg Ala Tyr
1               5                   10                  15

<210> SEQ ID NO 4
<211> LENGTH: 20
<212> TYPE: DNA
<213> ORGANISM: Artificial Sequence
<220> FEATURE:
<223> OTHER INFORMATION: Synthetic construct

<400> SEQUENCE: 4
cctcacttca ctgcactgta                                           20

<210> SEQ ID NO 5
<211> LENGTH: 20
<212> TYPE: DNA
<213> ORGANISM: Artificial Sequence
<220> FEATURE:
<223> OTHER INFORMATION: Synthetic construct

<400> SEQUENCE: 5
tgaacctcag ctacaaacag                                           20

<210> SEQ ID NO 6
<211> LENGTH: 19
<212> TYPE: DNA
<213> ORGANISM: Artificial Sequence
<220> FEATURE:
<223> OTHER INFORMATION: Synthetic construct

<400> SEQUENCE: 6
cccagcagac ttcacatgt                                            19

<210> SEQ ID NO 7

```
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
tcgctgagct gaaacaaatg                                          20

<210> SEQ ID NO 8
<211> LENGTH: 16
<212> TYPE: DNA
<213> ORGANISM: Artificial Sequence
<220> FEATURE:
<223> OTHER INFORMATION: Synthetic construct

<400> SEQUENCE: 8
cccagagcaa gagagg                                              16

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
caggttttct ttccctagct                                          20

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
tggtggtagg aagagtaaag                                          20

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
cctcccattt ccctcgtttt                                          20

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
cccttcttga aggtttacac                                          20

<210> SEQ ID NO 13
<211> LENGTH: 16
<212> TYPE: DNA
<213> ORGANISM: Artificial Sequence
<220> FEATURE:
<223> OTHER INFORMATION: Synthetic construct

<400> SEQUENCE: 13
```

```
gtccagacgc aggatg                                                   16

<210> SEQ ID NO 14
<211> LENGTH: 18
<212> TYPE: DNA
<213> ORGANISM: Artificial Sequence
<220> FEATURE:
<223> OTHER INFORMATION: Synthetic construct

<400> SEQUENCE: 14
attggcaaag cgaagctg                                                 18

<210> SEQ ID NO 15
<211> LENGTH: 18
<212> TYPE: DNA
<213> ORGANISM: Artificial Sequence
<220> FEATURE:
<223> OTHER INFORMATION: Synthetic construct

<400> SEQUENCE: 15
cagaaaacgg aagcccaa                                                 18

<210> SEQ ID NO 16
<211> LENGTH: 18
<212> TYPE: DNA
<213> ORGANISM: Artificial Sequence
<220> FEATURE:
<223> OTHER INFORMATION: Synthetic construct

<400> SEQUENCE: 16
acggaatttg aacagtat                                                 18

<210> SEQ ID NO 17
<211> LENGTH: 20
<212> TYPE: DNA
<213> ORGANISM: Artificial Sequence
<220> FEATURE:
<223> OTHER INFORMATION: Synthetic construct

<400> SEQUENCE: 17
tgcctcgctc tacggtgcct                                               20

<210> SEQ ID NO 18
<211> LENGTH: 21
<212> TYPE: DNA
<213> ORGANISM: Artificial Sequence
<220> FEATURE:
<223> OTHER INFORMATION: Synthetic construct

<400> SEQUENCE: 18
gatcaagtca agcgtgagtc g                                             21

<210> SEQ ID NO 19
<211> LENGTH: 20
<212> TYPE: DNA
<213> ORGANISM: Artificial Sequence
<220> FEATURE:
<223> OTHER INFORMATION: Synthetic construct

<400> SEQUENCE: 19
gtgggcctgg aggagagcga                                               20

<210> SEQ ID NO 20
<211> LENGTH: 18
<212> TYPE: DNA
```

```
<213> ORGANISM: Artificial Sequence
<220> FEATURE:
<223> OTHER INFORMATION: Synthetic construct

<400> SEQUENCE: 20
ttgcttggga aatccgag                                                 18

<210> SEQ ID NO 21
<211> LENGTH: 18
<212> TYPE: DNA
<213> ORGANISM: Artificial Sequence
<220> FEATURE:
<223> OTHER INFORMATION: Synthetic construct

<400> SEQUENCE: 21
tttcccctcg ctttctca                                                 18

<210> SEQ ID NO 22
<211> LENGTH: 16
<212> TYPE: DNA
<213> ORGANISM: Artificial Sequence
<220> FEATURE:
<223> OTHER INFORMATION: Synthetic construct

<400> SEQUENCE: 22
cccagagcaa gagagg                                                   16

<210> SEQ ID NO 23
<211> LENGTH: 18
<212> TYPE: DNA
<213> ORGANISM: Artificial Sequence
<220> FEATURE:
<223> OTHER INFORMATION: Synthetic construct

<400> SEQUENCE: 23
gctgtggctg ccattttt                                                 18

<210> SEQ ID NO 24
<211> LENGTH: 19
<212> TYPE: DNA
<213> ORGANISM: Artificial Sequence
<220> FEATURE:
<223> OTHER INFORMATION: Synthetic construct

<400> SEQUENCE: 24
ttgctggagt tgctggaag                                                19

<210> SEQ ID NO 25
<211> LENGTH: 18
<212> TYPE: DNA
<213> ORGANISM: Artificial Sequence
<220> FEATURE:
<223> OTHER INFORMATION: Synthetic construct

<400> SEQUENCE: 25
caggatagtt gcagtaat                                                 18

<210> SEQ ID NO 26
<211> LENGTH: 20
<212> TYPE: DNA
<213> ORGANISM: Artificial Sequence
<220> FEATURE:
<223> OTHER INFORMATION: Synthetic construct

<400> SEQUENCE: 26
ggctggagga atcggctggc                                               20
```

```
<210> SEQ ID NO 27
<211> LENGTH: 20
<212> TYPE: DNA
<213> ORGANISM: Artificial Sequence
<220> FEATURE:
<223> OTHER INFORMATION: Synthetic construct

<400> SEQUENCE: 27
agcctctcaa tggcgaacac                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic construct

<400> SEQUENCE: 28
ttgtccgccg ccacgaagtc                                              20

<210> SEQ ID NO 29
<211> LENGTH: 18
<212> TYPE: DNA
<213> ORGANISM: Artificial Sequence
<220> FEATURE:
<223> OTHER INFORMATION: Synthetic construct

<400> SEQUENCE: 29
tgcccgttca acatcctt                                                18

<210> SEQ ID NO 30
<211> LENGTH: 18
<212> TYPE: DNA
<213> ORGANISM: Artificial Sequence
<220> FEATURE:
<223> OTHER INFORMATION: Synthetic construct

<400> SEQUENCE: 30
tgcaggctga attcggtt                                                18

<210> SEQ ID NO 31
<211> LENGTH: 16
<212> TYPE: DNA
<213> ORGANISM: Artificial Sequence
<220> FEATURE:
<223> OTHER INFORMATION: Synthetic construct

<400> SEQUENCE: 31
gtccagacgc aggatg                                                  16

<210> SEQ ID NO 32
<211> LENGTH: 17
<212> TYPE: PRT
<213> ORGANISM: Artificial Sequence
<220> FEATURE:
<223> OTHER INFORMATION: Synthetic construct

<400> SEQUENCE: 32

Lys Gly Gly Gln Gly Phe Ser Tyr Pro Tyr Lys Ala Val Phe Ser Thr
 1               5                  10                  15

Gln
```

DEVICE AND USE THEREOF IN CELL EXPERIMENTS IN VITRO

This application is a U.S. National Phase Application of PCT/CN2015/096857 filed Dec. 9, 2015 which claims the priority from Chinese Patent Application CN201410850755.0 (filing date: Dec. 31, 2014, title of invention: "Device and Use thereof in Cell Experiments in vitro"), the contents of which are incorporated herein by reference.

REFERENCE TO A "SEQUENCE LISTING" SUBMITTED AS ASCII TEXT FILES VIA EFS-WEB

The Sequence Listing written in file 091922-001300US-1054563_SubSequenceListing.txt created on Nov. 6, 2017, 6,739 bytes, machine format IBM-PC, MS-Windows operating system, in accordance with 37 C.F.R. §§ 1.821- to 1.825, is hereby incorporated by reference in its entirety for all purposes.

TECHNICAL FIELD

The invention relates to a device useful in cell culture and use of this device in a cell experiment in vitro, and in particular to a device having a polydopamine layer-carboxymethyl chitosan layer-peptide layer structure and use thereof in a cell experiment in vitro.

BACKGROUND ART

Human induced pluripotent stem cells (hiPSCs) have almost the same characteristics, such as morphology, expandability, surface antigens, gene expression profile, methylation sites, etc., as those of human embryonic stem cells (hESCs). HiPSCs overcome ethical and moral confusions present in hESCs, increase the feasibility of autologous stem cell transplantation therapy, and solve the problem of the limited number of cells.

The culture of human pluripotent stem cells in vitro typically need to rely on mouse embryonic fibroblast (mEFs) or Matrigel. The mEFs culturing system has been gradually substituted by other culturing systems due to its complicated operation processes. Matrigel is a soluble basement membrane extract that obtained from the sarcoma of EHS (Engelbreth-Holm-Swarm) mouse, which can form a layer of thin membrane serving as the extracellular matrix on the surface of a growth substrate and enables human pluripotent stem cells to obtain desired adhesion and self-renewal in in vitro microenvironment established thereby (Xu, C., et al., Feeder-free growth of undifferentiated human embryonic stem cells, Nat Biotechnol, 2001, 19, 10, 971-4). However, since the Matrigel culturing system is heterologous and cannot ensure the consistency of products among different batches and there is an uncertainty of components thereof, it is not suitable for large-scale in vitro expansion of human pluripotent stem cells, which limits its application in clinical therapy. Therefore, a number of scientists have been devoted to the establishment of an in vitro culturing system of human pluripotent stem cells, which may replace Matrigel and has defined components.

First, researchers have sequentially found proteins such as fibronectin, vitronectin, laminin, etc., and certain specific parts of laminin may achieve in vitro self-renewal of human pluripotent stem cells. However, it is difficult for biological products such as proteins, etc., to be widely used in scientific research and clinical practice due to expensive price and batch inconsistency caused by physisorption. Therefore, in recent years, researchers have successfully developed few synthetic surfaces which support in vitro culturing and directional differentiation of human pluripotent stem cells and have significant advantages in terms of cost, batch stability, etc. Villa-Diaz L G et al., have formed a methacrylic acid ester type derivative—PMEDSAH coating—on polystyrene surface as well as a conditioned culture medium or a "StemPro" medium having defined chemical components so as to be capable of achieving the pluripotency maintenance of H9 hESCs (Villa-Diaz L G et al., Synthetic polymer coatings for long-term growth of human embryonic stem cells. Nature biotechnology. 2010; 28:581-3).

By forming a polyacrylic acid layer on the surface of a culture plate and grafting a peptide which promotes adhesion and proliferation of hESCs, Melkoumian Z et al., have experimentally demonstrated that pluripotency maintenance of about 10 passages of hESCs may be achieved on the surface functionalized and modified by the peptide of either Ac-KGGNGEPRGDTYRAY (SEQ ID NO:3) derived from bone sialoprotein (BSP) or Ac-KGGPQVTRGDVFTMP (SEQ ID NO:1) derived from vitronectin (VN) (Melkoumian Z et al., Synthetic peptide-acrylate surfaces for long-term self-renewal and cardiomyocyte differentiation of human embryonic stem cells. Nature biotechnology. 2010; 28:606-10).

However, these synthetic surfaces suffer from the following defects: (1) none has been verified to be capable of supporting somatic cells to be reprogrammed into hiPSCs; (2) most surfaces are not demonstrated to be effectively support a long-term pluripotency maintenance of various human pluripotent stem cells; (3) the production process is complicated; and (4) bio-inert or even bio-toxic components are used. Therefore, it is desirable to establish a simple, stable, and effective in vitro culturing system of human pluripotent stem cells having defined components by using compounds with good biocompatibility.

SUMMARY OF THE INVENTION

As a result of intensive investigations performed by the inventor with respect to the problems described above, it has been found that a polydopamine layer-carboxymethyl chitosan layer-VN peptide layer device is capable of regulating behaviors of human pluripotent stem cells. The invention is hereby completed.

That is, the invention is as follows.

1. A device, comprising:
a substrate,
a polydopamine layer attached to the substrate,
a carboxymethyl chitosan layer attached to the polydopamine layer, and
a peptide layer attached to the carboxymethyl chitosan layer;
wherein the peptide layer comprises a peptide A or a variant peptide thereof as follows;
peptide A: a peptide composed of the amino acid sequence of SEQ ID NO:1,
the variant peptide refers to:
(1) a peptide, which is composed of an amino acid sequence obtained by deletion, substitution, insertion, and/or addition of one or more amino acids in the amino acid sequence of the peptide A and has a function equivalent to that of the peptide A,
(2) a peptide, which is composed of an amino acid sequence having an amino acid homology of 70% or more with the amino acid sequence of the peptide A and has a function equivalent to that of the peptide A, and (3) a peptide, which is encoded by a nucleic acid which hybridizes with the nucleic acid encoding the amino acid sequence of the peptide A under stringent conditions and has a function equivalent to that of the peptide A.

2. The device according to item 1, wherein the distribution density of the peptide A in the peptide layer is 1-200 μg/cm$^2$.

3. The device according to item 1, wherein "a function equivalent to that of the peptide A" refers to being capable of regulating behaviors of human pluripotent stem cells, wherein the human pluripotent stem cells are human induced pluripotent stem cells or human embryonic stem cells, and regulating behaviors of human pluripotent stem cells refers to:

(1) inducing human somatic cells to be reprogrammed into human pluripotent stem cells, (2) allowing the adhesion of human pluripotent stem cells, and/or (3) allowing for long-term self-renewal of human pluripotent stem cells.

4. The device according to item 1, wherein the variant peptide of the peptide A is a VB peptide.

5. The device according to item 1, wherein the peptide layer further comprises a compound B having a function of promoting directional differentiation of human pluripotent stem cells.

6. The device according to item 5, wherein the distribution density of the compound B in the peptide layer is 1-200 μg/cm2.

7. The device according to item 5, wherein the compound B is BFP-1.

8. Use of the device according to any one of items 1-7 in a cell experiment in vitro, wherein the cell experiment in vitro comprises:

(1) inducing human somatic cells to be reprogrammed into human pluripotent stem cells, (2) allowing the adhesion of human pluripotent stem cells, and/or (3) allowing for long-term self-renewal of human pluripotent stem cells.

9. Use of the device according to any one of items 5-7 in promoting directional differentiation of human pluripotent stem cells.

10. A method for promoting directional differentiation of human pluripotent stem cells, comprising:

step B: culturing human pluripotent stem cells on the surface of the device of any one of claims 1-7 by using a directional induction medium.

11. The method according to item 10, further comprising:

step A: before the step B, culturing human pluripotent stem cells by using a medium capable of maintaining self-renewal of human pluripotent stem cells.

12. The method according to item 10, wherein the method is a method for promoting directional differentiation of human pluripotent stem cells into osteoblasts, and wherein the directional induction medium is an αMEM medium containing β-mercaptoethanol, dexamethasone, vitamin C, and fetal bovine serum.

13. The method according to item 10, wherein the method is a method for promoting directional differentiation of human pluripotent stem cells into neural precursor cells, the directional induction medium is an N2B27 culture broth supplemented with neural growth factors NGF and rmNoggin.

14. The method according to item 10, wherein the method is a method for promoting directional differentiation of human pluripotent stem cells into cardiac muscle cells, which comprises culturing human pluripotent stem cells by using a MEF-CM medium containing bFGF for 2-3 days, replacing with a RPMI+B27 medium on the first day of induction, adding Activin A and culturing for 24 h, adding BMP 4 and bFGF on the second day of induction and maintaining for four days without replacing medium, and replacing with a RPMI+B27 medium containing 50 ng/ml VEGF165 and continuing to culture.

15. The method according to item 10, wherein the method is a method for promoting directional differentiation of human pluripotent stem cells into dental epithelial cells, and wherein the directional induction medium is a DMEM/F12 medium containing N2, BMP-4, and RA.

16. The method according to item 10, wherein the method is a method for promoting directional differentiation of human pluripotent stem cells into hepatocytes, which comprises culturing human pluripotent stem cells for 3 days by using a RPMI/B27 induction medium supplemented with Activin A, then culturing for 4 days by using a RPMI/B27 induction medium supplemented with BMP2 and FGF4, culturing for 3 days by using a RPMI/B27 induction medium supplemented with Activin A, culturing for 6 days by using a RPMI/B27 induction medium supplemented with HGF and KGF, and culturing for 8 days by using an induction medium, which is a hepatocyte culture medium supplemented with SINGLEQUOTS™ (EGF free) and Oncostatin-M.

Effect of the Invention

1. All of the materials constituting the device have a good biocompatibility, and a system for regulating the fate of human pluripotent stem cells is established, which has defined chemical components, contains no exogenous substances and is safe.

2. It is possible to provide different biological functions to the system by grafting different functional peptides.

3. The polydopamine layer-carboxymethyl chitosan layer-peptide layer structure may be provided on the surface of various substrate materials, such as cell culture plates, implants, etc. This arrangement may be performed under conventional conditions, the steps are relatively simple and feasible, and do not require special apparatuses and high temperature, high pressure and the like, which complies with the requirements for GMP. Also, the production process avoids the use of chemicals which are toxic to organisms, and the process is more environmentally friendly.

4. The production process of this system only involves chemical reactions, and has a higher batch-to-batch stability compared to Matrigel and physisorption of proteins.

5. It is possible to promote directional differentiation of human pluripotent stem cells into different types of cells by using different directional induction culture media.

DESCRIPTION OF EMBODIMENTS

Figure 1:
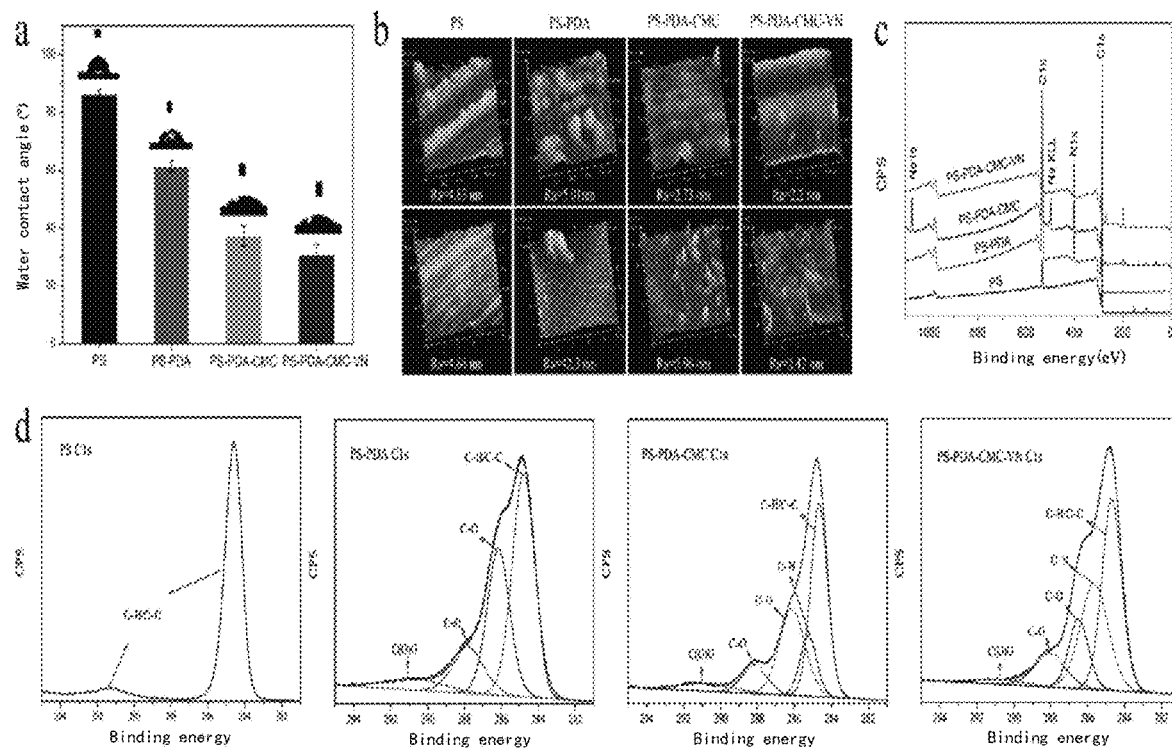
FIG. 1 illustrates the characterization of the PS surface sequentially modified by PDA/CMC/VN. (a) The change in the contact angle of the PS surface modified by PDA-CMC-VN; (b) XPS results; (c) AFM study—the change in the surface morphology of the PS surface in PDA-CMC-VN modification, wherein scan ranges are 1 μm×1 μm (top panel) and 5 μm×5 μm (bottom panel); (d) high resolution XPS spectrum of element C of PS, PS-PDA, PS-PDA-CMC, and PS-PDA-CMC-VN.

Scientific terms referred in this specification have the same meaning as commonly understood by the person skilled in the art, and the definition in this specification shall be referred to where a conflict exists.

Device

An aspect of the invention provides a device (also referred to as the device of the invention), comprising:

a substrate, a polydopamine layer attached to the substrate, a carboxymethyl chitosan layer attached to the polydopamine layer, and a peptide layer attached to the carboxymethyl chitosan layer;

wherein the peptide layer comprises a peptide A or a variant peptide thereof as follows;

peptide A: a peptide composed of the amino acid sequence of SEQ ID NO:1, the variant peptide refers to:

(1) a peptide, which is composed of an amino acid sequence obtained by deletion, substitution, insertion, and/or addition of one or more amino acids in the amino acid sequence of the peptide A, and has a function equivalent to that of the peptide A, (2) a peptide, which is composed of an amino acid sequence having an amino acid homology of 70% or more with the amino acid sequence of the peptide A, and has a function equivalent to that of the peptide A, and (3) a peptide, which is encoded by a nucleic acid which hybridizes with the nucleic acid encoding the amino acid sequence of the peptide A under stringent conditions, and has a function equivalent to that of the peptide A.

The device of the invention may be used in cell experiments in vitro or cell culture. In this specification, a cell experiment in vitro refers to: (1) inducing human somatic cells to be reprogrammed into human pluripotent stem cells, (2) allowing the adhesion of human pluripotent stem cells, and/or (3) allowing for long-term self-renewal of human pluripotent stem cells.

1. Substrate

The material used as the substrate of the device of the invention is not particularly limited, and those typically used as cell culture surfaces may be used, including for example, polystyrene, polydimethylsiloxane, glass, etc. As a substrate, for example, a cell culture plate may be used, or an implant (made of titanium or polyether ether ketone) may be used.

2. Polydopamine Layer

Dopamine (DA) is a biological neurotransmitter in vivo. When a substrate material is immersed in a buffer containing dopamine, dopamine will be deposited on the surface of the substrate material by oxidation polymerization so as to form a polydopamine layer on the surface of the substrate material.

The molecular weight of polydopamine (PDA) constituting the polydopamine layer is not particularly limited. The molecular weight of polydopamine may be controlled by a conventional method. For example, 0.01-100 g/L of dopamine solution reacts at 5-90° C. for 1 minute to 72 hours.

3. Carboxymethyl Chitosan Layer

Carboxymethyl chitosan (CMC) is one of the most important derivatives of chitosan, and similar to glycosaminoglycan (GAG), which is an extracellular matrix component, it has a good biocompatibility.

Through peptide fluorescein labeling study, the inventors have found that a VN peptide may be grafted on a PDA layer, but the resulting device cannot promote the adhesion of cells.

Surprisingly, the inventors have found that the resulting device is conferred with a function of regulating behaviors of human pluripotent stem cells in the case that a CMC layer is provided as a bridge between a PDA layer and a VN peptide layer. The weight average molecular weight of carboxymethyl chitosan used in the invention may be 1,000-200,000 g/mol, preferably 10,000-100,000 g/mol, more preferably 60,000-80,000 g/mol, as measured by a gel permeation chromatography and with reference to "Pharmacopoeia of the People's Republic of China". For example, the weight average molecular weight of the carboxymethyl chitosan in the CMC layer of the PDA-CMC-VN device prepared in Examples is 83,550 g/mol.

The carboxymethyl chitosan comprises an amino group and a carboxyl group, wherein a chemical bond may be formed between the amino group and polydopamine. The chemical bond between carboxymethyl chitosan and polydopamine may be achieved by a chemical reaction known in the art, for example, by Michael addition and Schiff base reaction. For example, a certain amount of a 0.1 wt %-30 wt % CMC solution may be added to a substrate of a polydopamine layer and reacts at 5 to 60° C. for 1 h-72 h, and a polydopamine-CMC substrate layer may be obtained.

4. Peptide Layer

The peptide layer shall comprise peptide A or a variant thereof as follows, and may also comprise other components as required (peptides, proteins, nucleic acids, small molecule compounds, etc.), as long as the device of the invention can exert the function of regulating behaviors of human pluripotent stem cells.

The peptide A is a peptide composed of the amino acid sequence of SEQ ID NO:1, and is referred to as VN peptide, which has an amino acid sequence of SEQ ID NO:1: KGGPQVTRGDVFTMP. The VN peptide is derived from vitronectin (VN). It has been reported that pluripotency maintenance of about 10 passages of hESCs may be achieved by forming a polyacrylic acid layer on the surface of a culture plate and grafting Ac-KGGNGEPRGDTYRAY (SEQ ID NO:3) derived from bone sialoprotein (BSP) and this VN peptide with N-terminal acetylated (Melkoumian Z et al., Synthetic peptide-acrylate surfaces for long-term self-renewal and cardiomyocyte differentiation of human embryonic stem cells. Nature biotechnology. 2010; 28:606-10).

It has been demonstrated by the study of the invention that the resulting device cannot promote the adhesion of cells when this VN peptide is directly grafted on the PDA layer. However, the resulting device is conferred with a function of regulating behaviors of human pluripotent stem cells in the case that a CMC layer is provided as a bridge between a PDA layer and a VN peptide layer.

The variant of the peptide A includes:

(1) a peptide, which is composed of an amino acid sequence obtained by deletion, substitution, insertion, and/or addition of one or more amino acids in the amino acid sequence of the peptide A, and has a function equivalent to that of the peptide A.

In this specification, relative to the variant peptide, peptide A refers to the peptide A described above.

In this specification, "a function equivalent to that of the peptide A" refers to any one, any two, or all of the following functions when the peptide A in the device of the invention is replaced with a variant peptide of the peptide A:

(i) inducing human somatic cells to be reprogrammed into human pluripotent stem cells, (ii) allowing the adhesion of human pluripotent stem cells, and/or (iii) allowing for long-term self-renewal of human pluripotent stem cells.

In the variant peptides, the amino acid substitution may be a conservative substitution. That is, a specific amino acid residue is replaced with a residue having a similar physicochemical property. Non-limiting examples of conserved substitutions include substitutions between amino acid residues containing aliphatic groups (for example, mutual substitutions between Ile, Val, Leu, and Ala), substitutions between polar residues (for example, mutual substitutions between Lys and Arg, between Glu and Asp, and between Gln and Asn), etc. In this specification, "one or more amino acids" refers to amino acids to the extent that deletion, substitution, insertion, and/or addition can be achieved by an artificially synthetic method, for example, 1-20 amino acids, preferably 1-15 amino acids, more preferably 1-10 amino acids, more preferably 1-8 amino acids, more preferably 1-2 amino acids, more preferably 1 amino acid.

Whether the variant peptide has a function equivalent to that of the peptide A may be determined by replacing the peptide A in the device of the invention with a variant peptide thereof and investigating whether the resulting device has any one, any two, or all of the above functions (i)-(iii).

The variant of the peptide A comprises:

(2) a peptide, which is composed of an amino acid sequence having an amino acid homology of 70% or more, preferably 80% or more, more preferably 90% or more, more preferably 95% or more, more preferably 97% or more, more preferably 98% or more, more preferably 99% or more with the amino acid sequence of the peptide A, and has a function equivalent to that of the peptide A.

The homology % between two amino acid sequences may be determined by visual inspection and mathematical calculation. Alternatively, the homology percentage between two peptide sequences may be determined by performing sequence information comparison by using a GAP computer program available from University of Wisconsin Genetics Computer Group (UWGCG) based on the algorithm of Needleman, S. B. and Wunsch, C. D. (J. Mol. Bol., 48: 443-453, 1970). Preferred default parameters of the GAP program include: (1) a scoring/matrix, blosum62, as described by Henikoff, S. and Henikoff, J. G. (Proc. Natl. Acad. Sci. USA, 89:10915-10919, 1992); (2) a gap penalty of 12; (3) a continued gap penalty of 4; and (4) no penalty for end gaps. Other programs, which are used for performing sequence comparison by those skilled in the art, may also be used. With respect to the homology percentage, for example, a BLAST program may be used to compare and determine the sequence information, as described by Altschul et al. (Nucl. Acids. Res., 25, p. 3389-3402, 1997). This program is available on the Internet at the web site of the National Center for Biotechnology Information (NCBI) or the DNA Data Bank of Japan (DDBJ). The details of various conditions (parameters) for homology search by using the BLAST program are shown on the same web sites, and default values are commonly used for search although a part of settings may be changed as appropriate. Furthermore, the homology % between two amino acid sequences may be determined by using a program such as genetic information processing software GENETYX Ver. 7 (produced by GENETYX) or using an algorithm such as FASTA. In this case, default values may be used for search.

The variant of the peptide A comprises:

(3) a peptide, which is encoded by a nucleic acid which hybridizes with the nucleic acid encoding the amino acid sequence of the peptide A under stringent conditions, and has a function equivalent to that of the peptide A.

In this specification, "stringent conditions" refer to conditions where so-called specific hybrids are formed and non-specific hybrids are not formed. The examples of stringent conditions include those conditions where highly homologous DNAs hybridize with each other, for example, DNAs having a homology of no less than 80%, preferably having a homology of no less than 90%, more preferably having a homology of no less than 95%, still more preferably having a homology of no less than 97%, particularly preferably having a homology of no less than 99% hybridize with each other, and DNAs having a homology less than those described above do not hybridize with each other; or typical washing conditions in Southern hybridization, i.e., washing once, preferably twice or 3 times at a salt concentration and temperature corresponding to 1×SSC, 0.1% SDS at 60° C., preferably 0.1×SSC, 0.1% SDS at 60° C., and more preferably 0.1×SSC, 0.1% SDS at 68° C.

As a variant of the peptide A (VN peptide), a VB peptide may be exemplified. The VB peptide has an amino acid sequence of KGGPQVTRGDTYRAY (SEQ ID NO:2, and this peptide may be acetylated, which is Ac-KGG-PQVTRGDTYRAY (SEQ ID NO:2)). The VB peptide is an artificial peptide designed by the inventors, and it is shown by experimental results that it has a function equivalent to that of VN peptide and is not inferior to the VN peptide in terms of properties.

To achieve the function of the device of the invention, the distribution density of the peptide A or a variant thereof should be above a certain value, for example, 1 $\mu g/cm^2$ or more, preferably 10 $\mu g/cm^2$ or more, more preferably 20 $\mu g/cm^2$ or more, more preferably 30 $\mu g/cm^2$ or more, and more preferably 40 $\mu g/cm^2$ or more. Furthermore, the distribution density of the peptide A or a variant thereof is not particularly limited, and may be, for example, 200 $\mu g/cm^2$ or less, 150 $\mu g/cm^2$ or less, 100 $\mu g/cm^2$ or less, 80 $\mu g/cm^2$ or less, or 60 $\mu g/cm^2$ or less, in view of the operability.

The carboxymethyl chitosan comprises an amino group and a carboxyl group, wherein the carboxyl group may be grafted to a peptide. The grafting of carboxymethyl chitosan to a peptide may be achieved by a chemical reaction known in the art. For example, the polydopamine-carboxymethyl chitosan surface is immersed into an activating agent solution (for example, 20 mg/ml N-hydroxysuccinimide and 20 mg/ml 1-(3-dimethylaminopropyl)-3-ethylcarbodiimide hydrochloride, pH=5.6, morpholinoethane sulfonic acid buffer) and reacts at room temperature for 10-1000 min, then reacts with a 0.1-100 mM VN peptide solution at 4° C. overnight. As a result, a polydopamine-carboxymethyl chitosan-VN peptide modified surface for culturing human pluripotent stem cells may be obtained by Michael addition and Schiff base reaction.

Furthermore, as a method for allowing the distribution density of the peptide A or a variant thereof to be up to 1 $\mu g/cm2$ or more, the concentration of reaction solution of the peptide A should be 0.25 mM or more, preferably 1 mM or more.

In one preferred embodiment, the peptide layer may further comprise a compound B having a function of promoting directional differentiation of human pluripotent stem cells, and in combination with a specific medium with defined components, in vitro directional induction differentiation of human pluripotent stem cells may be achieved. The compound B may be a peptide, a protein, a nucleic acid, or a small molecule compound. The compound B and the specific medium are not particularly limited, as long as they have a function of promoting directional differentiation of human pluripotent stem cells. A suitable compound B and a suitable directional induction culture medium may be selected by the person skilled in the art according to the requirements of directional differentiation. For example, (1) the peptide layer is grafted with a BFP-1 peptide and an αMEM medium containing β-mercaptoethanol, dexamethasone, and vitamin C is comprised to directionally induce osteogenic differentiation of human pluripotent stem cells;

(2) the peptide layer is grafted with a neural growth factor (NGF) and a N2B27 culture broth supplemented with 100 ng/ml rmNogginis to directionally induce human pluripotent stem cells into neural precursor cells. Further, the neural precursor cells are cultured in a N2B27 culture broth containing a neural factor, BDNF, GDNF, CNTF, IGF1, and cAMP and may directionally differentiate into neuron cells; or the neural precursor cells are seeded on a poly-L-ornithine substrate and may be directionally induced to differentiate into oligodendrocytes by using a DEME/F12 culture broth containing NI, biotin, PDGF-AA, NT3, cAMP, bFGF, and IGF1.

Therefore, the invention further provides a method for promoting directional differentiation of human pluripotent stem cells, comprising step B: culturing human pluripotent stem cells on the surface of the device of the invention by using a directional induction medium. By culturing human pluripotent stem cells on the surface of the device of the invention by using a directional induction medium, directional differentiation of human pluripotent stem cells may be promoted. Here, the directional induction culture medium refers to a medium having a function of promoting directional differentiation of human pluripotent stem cells. It is known in the art which kind of directional induction culture medium may promote directional differentiation of human pluripotent stem cells into a specific type of cells. For example, an αMEM medium containing β-mercaptoethanol, dexamethasone, vitamin C, and fetal bovine serum is used in the differentiation of human pluripotent stem cells into osteoblasts; and a DMEM/F12 medium containing N2, BMP-4, and RA may promote directional differentiation of human pluripotent stem cells into dental epithelial cells, etc.

Preferably, the above method for promoting directional differentiation of human pluripotent stem cells may further comprise step A: before the step B, culturing human pluripotent stem cells by using a medium capable of maintaining self-renewal of human pluripotent stem cells. By culturing human pluripotent stem cells by using a medium which can maintain self-renewal of human pluripotent stem cells, proliferation of human pluripotent stem cells is allowed.

Conventional operational manners and culture conditions for culturing human pluripotent stem cells by using a directional induction culture medium to allow directional differentiation thereof and culturing human pluripotent stem cells by using a medium which can maintain self-renewal of human pluripotent stem cells to allow proliferation thereof are known to those skilled in the art. In the method for promoting directional differentiation of human pluripotent stem cells of the invention, these conventional operational manners and culture conditions may be suitably used, in addition to the use of the device of the invention as a culture surface.

A suitable compound B and a suitable directional induction culture medium may be selected by the person skilled in the art according to the requirements of directional differentiation. For example, (1) the peptide layer is grafted with a BFP-1 peptide and an αMEM medium containing β-mercaptoethanol, dexamethasone, and vitamin C is comprised to directionally induce osteogenic differentiation of human pluripotent stem cells;

(2) the peptide layer is grafted with a neural growth factor (NGF) and a N2B27 culture broth supplemented with 100 ng/ml rmNoggin is comprised to directionally induce human pluripotent stem cells into neural precursor cells. Further, the neural precursor cells are cultured in a N2B27 culture broth containing a neural factor, BDNF, GDNF, CNTF, IGF1, and cAMP and may directionally differentiate into neuron cells; or the neural precursor cells are seeded on a poly-L-ornithine substrate and may be directionally induced to differentiate into oligodendrocytes by using a DEME/F12 culture broth containing NI, biotin, PDGF-AA, NT3, cAMP, bFGF, and IGF1.

(3) Human pluripotent stem cells surface-cultured in the invention are cultured with a MEF-CM medium containing bFGF for 2-3 days. A RPMI+B27 medium is replaced on the first day of induction, and Activin A is added to allow culturing for 24 h. BMP 4 and bFGF are added on the second day to maintain for four days without replacing medium. Subsequently, it is replaced with a RPMI+B27 medium containing 50 ng/ml VEGF165 and the culture continues to enable directional differentiation into cardiac muscle cells.

(4) Human pluripotent stem cells surface-cultured in the invention may be directionally induced into dental epithelial cells by using a DMEM/F12 medium containing N2, BMP-4, and RA.

(5) Human pluripotent stem cells surface-cultured in the invention may be directionally induced into hepatocyte-like cells by using media containing different compounds at different stages. At the first stage, a basal medium, which is RPMI/B27 (minus insulin), is formulated, and cytokine Activin A is added, and culture is performed for 3 days; at the second stage, the basal medium is RPMI/1327 (complete with Insulin), and cytokines BMP2 and FGF4 are added, and culture is performed for 4 days; at the third stage, the basal medium is RPMI/B27 (complete with Insulin), and cytokines HGF and KGF are added, and culture is performed for 6 days; and at the fourth stage, the basal medium is a hepatocyte culture medium supplemented with SINGLE-QUOTS™ (EGF free), and cytokine Oncostatin-M is added, and culture is performed for 8 days.

The distribution density of the compound B is not particularly limited, as long as it can exert a function of promoting directional differentiation of human pluripotent stem cells, and is preferably at least 1 μg/cm² or more, preferably 10 μg/cm² or more, more preferably 20 μg/cm² or more, more preferably 30 μg/cm² or more, and more preferably 40 μg/cm² or more.

As a method for grafting the compound B on carboxymethyl chitosan, a method which is the same as the method for grafting the peptide A may be used.

The peptide may be suitably obtained by using a well-known method, such as (1) a chemical synthesis method, or (2) an enzymatic reaction synthesis method, etc., wherein chemical synthesis is simpler. In the case of chemically synthesizing the peptide of the invention, the synthesis or semi-synthesis of this peptide is performed by using a peptide synthesizer. As a chemical synthesis method, for example, a peptide solid-phase synthesis method, etc., may be exemplified. The peptide synthesized in this way may be purified by using a conventional measure, for example, ion exchange chromatography, reverse-phase high-performance liquid chromatography, affinity chromatography, etc. The peptide solid-phase synthesis method and the subsequent peptide purification are all well known in the art.

Furthermore, in the case of producing the peptide of the invention by enzymatic reaction, the method as described in the pamphlet of International Publication No. WO2004/011653 may be used, for example. That is, the production may be performed by performing a reaction between an amino acid or a dipeptide obtained by esterification or amidation of the carboxyl terminus of an amino acid or a dipeptide and an amino acid in free state (e.g., an amino acid with the carboxyl group protected) in the presence of a peptide synthase to generate a dipeptide or a tripeptide. As a peptide synthase, a culture of microorganisms having the ability of generating peptides, a bacterial cell of microorganism isolated from this culture, a treated product of the bacterial cell of this microorganism, or a peptide synthase derived from this microorganism may be exemplified.

In particular, the commercialization of the chemical synthesis of peptides has been achieved, and professional companies of peptide synthesis may be readily assigned to synthesize the peptide.

Use of Device

Another aspect of the invention provides the use of the device of the invention in a cell experiment in vitro.

In this specification, a cell experiment in vitro refers to any one, any two, or all of the following items (1)-(3):

(1) inducing human somatic cells to be reprogrammed into human pluripotent stem cells, (2) allowing the adhesion of human pluripotent stem cells, and/or (3) allowing for long-term self-renewal of human pluripotent stem cells.

In this specification, human pluripotent stem cells refer to human induced pluripotent stem cells (hiPSCs) and human embryonic stem cell (hESCs).

In this specification, the adhesion of human pluripotent stem cells refers to the case that human embryonic stem cells and human induced pluripotent stem cells can adhere to the surface of a treated cell culture plate, rapidly spread upon adhesion, then begin mitoses, and rapidly enter the logarithmic growth phase.

In this specification, the self-renewal of human pluripotent stem cells refers to the case that a human pluripotent stem cell may generate two cells which are the same as the original cells by symmetric division. In this specification, the long-term self-renewal of human pluripotent stem cells refers to the case that human pluripotent stem cells still maintain the pluripotency after more than 20 passages of continuous subculturing in an in vitro microenvironmental system.

In one preferred embodiment, in the case that the device of the invention comprises the compound B described above, the device of the invention may be further used to promote directional differentiation of human pluripotent stem cells.

In this specification, the directional differentiation of human pluripotent stem cells refers to a process that the morphology, structure, and function of human pluripotent stem cells change under the action of related factors.

EXAMPLES

The invention will be illustrated by Examples below in details, but the invention is in no way limited by these Examples.

Example 1. Manufacture and Characterization of PDA-CMC-VN Device

The PDA-CMC-VN device manufactured below has a substrate (the surface of a cell culture plate), a polydopamine layer, a carboxymethyl chitosan layer, and a VN peptide layer, in sequence.

24 g of carboxymethyl chitosan was added to a blue-mouth bottle containing 800 ml of pure water and stirred overnight by using a thermostatic stirrer under a condition of 50° C. and 150 rpm to obtain a CMC solution having a mass fraction of 3%. After a filter paper rough filtration at a medium speed, a sterile CMC solution was obtained by sequentially filtering with 0.45 μm and 0.22 μm filtration membranes in a super clean bench. 0.2424 g of tris(hydroxymethyl) aminomethane hydrochloride was placed in a beaker containing 200 ml of pure water and uniformly stirred with a burette, and the pH of the solution was adjusted to 8.5 with 1 mol/L hydrochloric acid. 0.4 g of dopamine powder was added to this buffer and uniformly stirred with a burette. After filtration with a 0.22 μm filtration membrane in a super clean bench, it was added to a Corning 6-well cell culture plate (5 ml volume per well), and placed in a thermostatic shaker (70 rpm) at 37° C. after enclosing with a Parafilm wrap and reaction was performed for 16 h. After washing with sterile pure water in a super clean bench for 3 times, 5 ml of pure water was added to each well, ultrasonic treatment was performed for 5 min after enclosing with a Parafilm wrap, then 5 ml of a CMC solution was added to each well after washing with pure water in a super clean chamber once, and reaction was performed for 24 h by placing in a thermostatic shaker (70 rpm) at 37° C. after enclosing with a Parafilm wrap. Thereafter, the interior of the super clean bench was rinsed with sterile pure water for 3 times, dried, and irradiated with ultraviolet for 1 h.

In the super clean bench, 5 mg of a VN peptide was dissolved in 3.1 ml of DPBS buffer to obtain a 1 mM VN peptide solution. 19.52 g of morpholinoethane sulfonic acid was dissolved in 1000 ml of pure water and uniformly stirred with a glass rod, and the pH was adjusted to 5.6 with a saturated sodium hydroxide solution. 0.8 g of N-hydroxysuccinimide and 0.8 g of 1-(3-dimethylaminopropyl)-3-ethylcarbodiimide hydrochloride were dissolved in 20 ml of a morpholinoethane sulfonic acid buffer respectively and uniformly mixed. After filtration in a super clean bench with a 0.22 μm filtration membrane, it was added to a Corning 6-well cell culture plate (3 ml volume per well), and reaction was performed at room temperature for 40 min. After washing with sterile pure water for 3 times, 1 ml of VN peptide solution was added to each well, which was enclosed with a Parafilm wrap at 4° C. overnight and rinsed with sterile pure water 3 times to obtain a polydopamine-carboxymethyl chitosan-VN peptide modified cell culture plate. Chemical and morphological changes of the surface of the cell culture plate modified by a PDA-CMC-VN coating layer were studied by using X-ray photoelectron spectroscopy (XPS), contact angle, and atomic force microscope (AFM).

Furthermore, we performed a quantitative study on the surface-grafted VN peptide by using a VN peptide labeled by fluorescin FITC (FITC-KGGPQVTRGDVFTMP (SEQ ID NO:1)). First, FITC-VN solutions of concentrations of 0.2 mM and 2 mM were formulated with a 1:1 mixed liquid of acetonitrile and pure water under protection from light, and 2 ul 0.2 mM, 5 ul 0.2 mM, 1 ul 2 mM, 2 ul 2 mM, 4 ul 2 mM, 8 ul 2 mM, 16 ul 2 mM (4 wells for each group) were then added to a Corning 96-well plate, respectively. After drying under protection from light, fluorescence values were measured by using a full-wavelength microplate reader with excitation light of 488 nm and absorption light of 538 nm to establish a fluorescence-density standard curve. Thereafter, 1 mM FITC-VN solution was formulated, grafted to an activated PS-PDA-CMC surface by using the method described above, and washed with pure water for 3 times, and fluorescence values were measured under the same conditions.

As shown in FIG. 1a, before modification, PS exhibits a typical water contact angle value)(86.36±1.67°, the contact angles of surfaces modified by PDA/CMC/VN were reduced to 61.54±1.70°, 41.48±7.16°, and 30.88±3.52°, respectively. We used an atomic force microscope to measure changes in surface morphology of PS surfaces modified by PDA/CMC/VN peptides, respectively. We selected two scan ranges, 1 µm×1 µm and 5 µm×5 µm, and AFM measurement results were shown in FIG. 1b, respectively. The results of 1 µm×1 µm showed that the unmodified PS surface is relatively smooth (Ra=4.83 nm). After modified by polydopamine, we could see typical polydopamine particles on the surface of this substrate, and the Ra value was increased to 5.01 nm correspondingly. After further modified by CMC and VN peptides, we found that the Ra value of the surface exhibited a declining tendency, and a highly smooth surface was finally obtained (Ra=2.20 nm). When the scan range of AFM was enlarged to 5 µm×5 µm, similar AFM measurement results were also found. This modification process was further characterized by using XPS (see FIGS. 1c-d). The newly found N element peak demonstrated the formation of the PDA layer, and the presence of the Na element peak and the "C—N" bond illustrated that CMC was successfully covalently bonded to the PDA layer. Finally, after grafting with the VN peptide, the peptide bonds contained thereby allowed the content of "C—N" to be increased. The characterization results described above illustrated that the PDA-CMC-VN surface we developed could be covalently bonded to the surface of the PS culture plate.

Furthermore, we measured that the fluorescence intensity of the surface of the PS-PDA-CMC-FITCVN modified 12-well plate was 399.695±73.65291. As can be known from the results of the standard curve of a 96-well plate, the grafting density of the VN peptide on the surface was 51.75±9.53 ug/cm2.

Example 2. PDA-CMC-VN Device Allowed Adhesion of Human Pluripotent Stem Cells

Cell Culture

H1 hESCs and H9 hESCs were purchased from WiCell Research Institute by Guangzhou Institute of Biomedicine and Health, Chinese Academy of Sciences, and were then provided as presents. hiPSCs lines (hNF-C1 derived from human skin cells and UMC-C1 derived from human mesenchymal stem cells) were both obtained from Guangzhou Institute of Biomedicine and Health, Chinese Academy of Sciences by lentiviral reprogramming method, and were then provided as presents. These human pluripotent stem cell lines were cultured in culture plates coated with Matrigel (BD Biosciences, Canada), and components used in the media are defined MTESR™1 (StemCell Technologies, Canada). The cell culture was performed in an incubator at 37° C., 100% humidity, and 5% CO2. Matrigel was diluted with DMEM/F12 at 1:80 on ice, added to a 6-well plate with a 1 mlvolume per well, and incubated at 37° C. for 1 h or more. Medium was replaced for cells every day, and the cells were digested with 0.5 mM EDTA at 37° C. for 4-5 min every 3-4 days and passaged at a ratio of 1:3.

The PDA-CMC-VN modification supports the culture of human pluripotent stem cells on the surface of different substrates.

As described above, PDA/VN and PDA-CMC/VN modified 6-well culture plates grafted with 1 mM VN peptides were produced, while quantitative studies were performed by using FITC-labeled fluorescent peptides. hNF-C1 hiPSCs were digested into single cells with 0.25% trypsin/EDTA (Stem Cell Technologies, Canada) and seeded onto PDA/VN and PDA-CMC-VN modified 6-well plates at a density of 23,500 cells/cm-2, and a culture plate pre-plated with Matrigel was used as a control. Fresh media were replaced every day until the fourth day, and a CCK8 cell number counting kit (Dojindo, Japan) was used to measure the cell number in each well. Each group included three wells in parallel, and the absorbance value of each well was measured for three times. The particular experimental method was as follows.

1. The experiment was performed under protection from light. A CCK8 reagent was added to a MTESR™1 medium at a ratio of 1:10 and uniformly mixed, and 1 ml was added to each well.
2. Reaction was performed in an incubator for 2 hours, 200 ul was taken from each well and was transferred to a 96-well plate, and the absorbance value was measured with a full-wavelength microplate reader (Model 680, Bio-Rad, Hercules, Calif.).

Furthermore, hNF-C1 hiPSCs cultured on Matrigel were digested with EDTA, and transferred to surfaces of different substrates (PS, glass, PDMS, and Ti) modified by PDA-CMC-VN at a ratio of 1:3. After culturing for 4 days, the cell morphology on the surfaces of the materials was observed by using an inverted microscope (Olympus CKX31SF, Japan) and an upright metallographic microscope (Olympus BX51M, Japan). In the meanwhile, cells were collected and the expression of Oct-4 was measured by flow cytometry.

Study on Cell Adhesion

H1 hESCs and hNF-C1 hiPSCs were selected to study the effect of the concentration of peptides, the method of digestion, and ROCK inhibitor Y-27632 on the adhesion of human pluripotent stem cells. First, a PDA/CMC modified 6-well plate was activated by NHS/EDC, 1 ml of VN peptide at different concentrations (0.25 mM, 0.5 mM, 0.75 mM, 1 mM) were added to wells, and reaction was performed at 4° C. overnight. On the second day, the culture plate grafted with the peptide was washed with a DMEM/F12 medium for three times, H1 hESCs and hNF-C1 human induced pluripotent cells cultured on Matrigel were digested into single cells with 0.25% Trypsin/EDTA, which were seeded at a density of 23,500 cells per square centimeter. At the same time, the cells were transferred onto Matrigel at the same density and taken as a control. Fresh media were replaced every day until the fourth day, a CCK8 kit was then used to measure the cell count in each well.

As described above, 1 mM VN was added to the activated PDA/CMC modified culture plate with 1 mlvolume per well, and a PDA-CMC-VN surface was produced for use in subsequent experiments related to human pluripotent stem cells. H1 hESCs and hNF-C1 hiPSCs were seeded onto the PDA-CMC-VN surface and the Matrigel surface in a form of single cells or clones (23,500 cells per square centimeter), respectively, to study the effect of the passage manner on the adhesion and the proliferation of human pluripotent stem cells. In the meanwhile, the effect of ROCK inhibitor Y-27632 was also studied. That is, 5 mM Y-27632 was added in one group and was not added in the other group. Fresh media were replaced every day until the fourth day, and a CCK8 kit was then used to measure the cell count in each well.

In the experiments described above, each group contained 3 wells in parallel, and the CCK8 reagent absorbance value of each well was measured for 3 times.

Experimental Results

Figure 2:
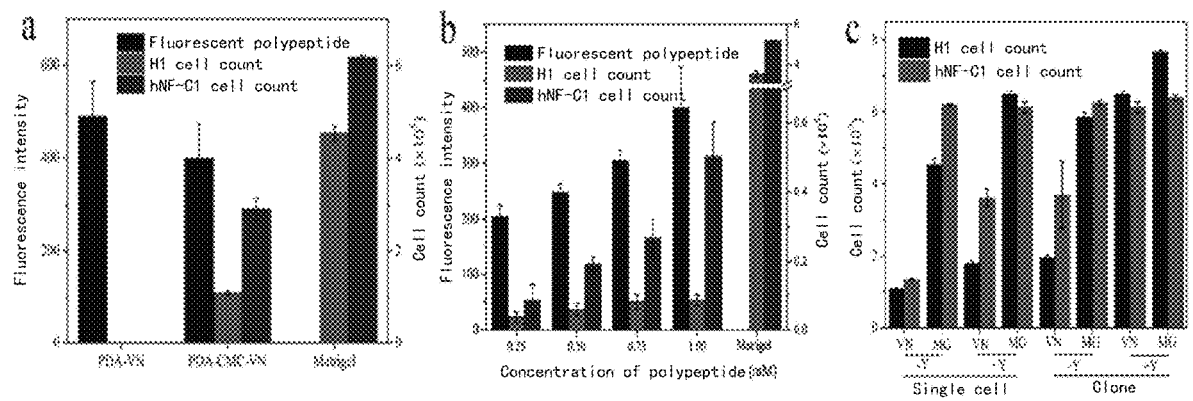
FIG. 2: (a) Comparison of amounts of peptides grafted on the PDA-VN surface and the PDA-CMC-VN surface by using FITC-VN peptide, and the effect on the cell numbers of H1 hESCs and hNF-C1 hiPSCs grown on the surfaces after four days. (b) The effect of the concentration of VN peptide on the adhesion and growth of H1 hESCs and hNF-C1 hiPSCs. (c) The effect of the digestion method and Y-27632 on the cell numbers of H1 hESCs and hNF-C1 hiPSCs cultured on the PDA-CMC-VN surface and the Matrigel surface on the fourth day.

As shown in FIG. 2a, although the fluorescent peptide experiment demonstrated that a large amount of VN peptide was successfully grafted to the polydopamine surface, adhered H1 hESCshESCs and hNF-C1 hiPSCs were not found, illustrating that this direct grafting manner was not feasible. Thus, we introduced carboxymethyl chitosan containing both an amino group and a carboxyl group, which was first covalently grafted to the polydopamine surface, and then the carboxyl group exposed on the surface was activated by a typical NHS/EDC reaction so as to graft the VN peptide. Interestingly, although the incorporation of CMC reduced the grafted amount of the VN peptide, both H1 human embryonic stem cells and hNF-C1 hiPSCs could well adhere to and grow on the surface of the PDA-CMC-VN modified culture plate, as demonstrated by experiments.

H1 hESCs and hNF-C1 hiPSCs were selected to study the effect of the concentration of peptides, the digestion manner, and ROCK inhibitor Y-27632 on the adhesion and the proliferation of human pluripotent stem cells on the surface of the PDA-CMC-VN modified culture plate. As shown in FIG. 2b, as the concentration of the VN peptide increased, the PDA-CMC-VN surface comprised more VN peptide. The cell count of hNF-C1 hiPSCs also gradually increased, but the cell count of H1 hESCs was not significantly changed, and both of them were significantly lower than that of the Matrigel control group ($p<0.01$). These results illustrated that the distribution density of the peptide should be above a certain value so as to achieve a long-term culturing and expansion on the PDA-CMC-VN surface. We further studied the promoting effect of the digestion manner and ROCK inhibitor Y-27632 on the adhesion and the growth of hPSCs. The addition of Y-27632 can significantly increase the cell numbers of H1 hESCs and hNF-C1 hiPSCs which were cultured on the PDA-CMC-VN surface for 4 days ($p<0.05$) despite of a digestion manner of single cells or clones. However, on the Matrigel surface, with respect to either single cells or clones, the promoting effect of Y-27632 is relatively significant for H1 hESCs but is not significant for hNF-C1 hiPSCs. Furthermore, we found that the cell numbers of H1 hESCs and hNF-C1 hiPSCs seeded in the form of clones were significantly greater than the cell numbers of those seeded in the form of single cells ($p<0.05$), after growing on the PDA-CMC-VN surface for four days, regardless whether Y-27632 was added or not. We surprisingly found that in combination with the digestion manner of EDTA and Y-27632, the cell count of hNF-C1 hiPSCs after growing on the PDA-CMC-VN surface for four days was close to that of Matrigel.

Example 3. PDA-CMC-VN Device Induced Reprogramming of Human Somatic Cells into Human Pluripotent Stem Cells The experiment of the reprogramming of human urine cells into human induced pluripotent stem cells was performed at Guangzhou Institute of Biomedicine and Health, Chinese Academy of Sciences. First, we successfully purified and obtained urine cells from the urine of a male patient suffering from Parkinson's disease. Non-integrating episomal vectors simultaneously encoding Oct-4 (POU5F1), Sox-2, SV40LT, and Klf-4 and MicroRNA MIR302-367 were transfected into 1.5 million urine epithelial cells by using an electroporation apparatus (AmaxaNucleofector II, Lonza, Switzerland) according to the operation manual. After transfection, cells were transferred to a 6-well plate with 3 wells modified by PDA-CMC-VN, and cultured with an E7 medium (Stem Cell) supplemented with sodium butyrate with medium replaced every other day. On the 14th day after transfection, the medium was replaced with MTESR™1 (Stem Cell) and culture continued, and clones were picked up after the 18th day. After culturing to 16th passage on the PDA-CMC-VN surface, the pluripotency of the resulting PDUE0304 hiPSCs was identified by using experiments of karyotype, flow cytometry, immunofluorescence, in vitro embryoid bodies, and teratoma.

Figure 3:
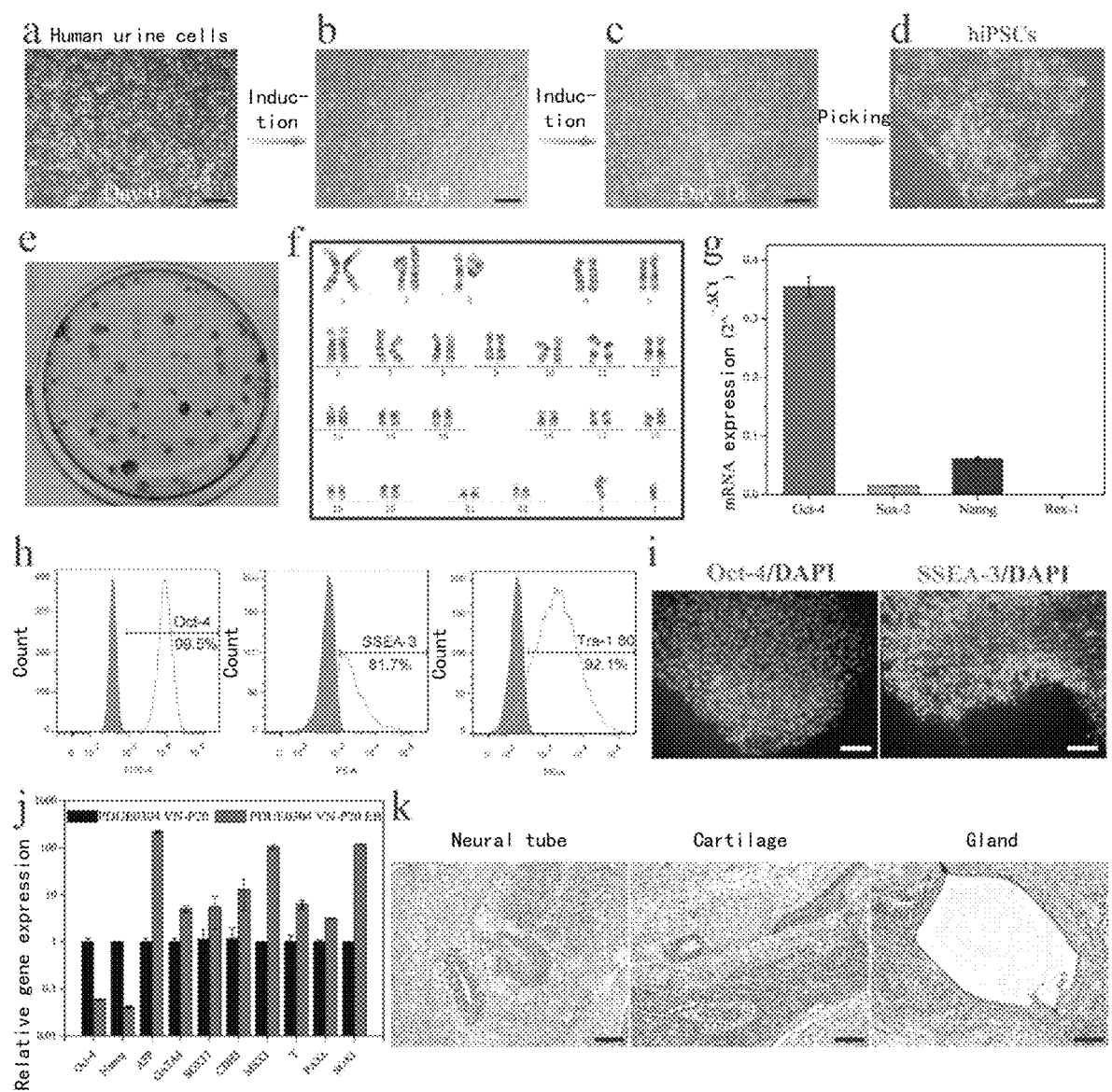
FIG. 3 illustrates the reprogramming process and the pluripotency identification of human urine cells. (a) The morphology of human urine cells before reprogramming. (b) Embryonic-stem-cell-like human induced pluripotent stem cell clones appeared on the PDA-CMC-VN surface on the 8th day of reprogramming. (c) Typical embryonic-stem-cell-like human induced pluripotent stem cell clones appeared on the surface on the 18th day of reprogramming. (d) The morphology of the 16th passage of PDUE0304 hiPSC clones cultured on the PDA-CMC-VN surface. (e) Human urine cells were AP-stained on the 18th day of reprogramming on a PDA-CMC-VN modified 6-well plate. (f) Karyotype analysis of cells. (g) The expression of pluripotency genes Oct-4, Sox-2, Nanog, and Rex-1 in cells was analyzed by RT-PCR. (h) The expression of surface markers Oct-4, SSEA-3, and Tra-1 60 in PDUE0304 hiPSCs cultured to P16 on the PDA-CMC-VN surface was detected by flow cytometry. (i) The expression of cell surface markers Oct-4 and SSEA-3 was detected by immunofluorescence. Scale: 100 μm. (j) The expression of the triploblastic marker genes of embryoid bodies formed by PDUE0304 hiPSCs was analyzed by quantitative RT-PCR. (k) Teratoma was formed in a NOD/SCID mouse after PDUE0304 hiPSCs were cultured to 16th passage on the PDA-CMC-VN surface, and was stained with hematoxylin-eosin. Scale: 200 μm.

Experimental results: a small number of embryonic-stem-cell-like hiPSCs clones appeared on the PDA-CMC-VN surface on the 8th day of reprogramming (see FIG. 3b). A large number of typical embryonic-stem-cell-like hiPSCs clones appeared on the surface when induction continued until the 18th day of reprogramming. We picked up one clone onto the Matrigel surface (see FIGS. 3c and e). As shown in FIG. 3d, PDUE0304 hiPSCs cultured to P16 on the PDA-CMC-VN surface exhibited a typical morphology of undifferentiated clones and had complete karyotypes (see FIG. 3f). It was demonstrated by quantitative RT-PCR that cells expressed pluripotency genes Oct-4, Nanog, and Sox-2 but did not express differentiation gene Rex-1 (see FIG. 3g). The results of flow cytometry and immunofluorescence showed that cells highly expressed pluripotency markers, such as Oct-4, SSEA-3, and Tra-1 60, etc. (see FIGS. 3h-i). Furthermore, it was demonstrated by in vitro embryoid body and teratoma experiments that PDUE0304 hiPSCs had the triploblastic differentiation potential (see FIGS. 3j-k). These results demonstrated that the device PDA-CMC-VN device we developed could support reprogramming of human somatic cells. To our knowledge, these experiments reported for the first time that the peptide modified surface with defined components could reprogram human somatic cells into hiPSCs, and which would certainly facilitate to the use of the artificially synthetic surface in human pluripotent stem cells.

Example 4. PDA-CMC-VN Device Allowed a Long-Term Self-Renewal of Human Pluripotent Stem Cells Long-Term Self-Renewal of Human Pluripotent Stem Cell Lines After human embryonic stem cells (H1, H9) and human induced pluripotent stem cell lines (hNF-C1, GZC2F6 and UMC-C1) cultured on Matrigel were digested with 0.5 mM EDTA under the condition of 37° C. for 4 minutes, clones were blown off with a MTESR™1 medium containing 5 μm of Y-27632 and transferred to a PDA-CMC-VN modified 6-well plate at a ratio of 1:3. On the second day, it was replaced with a medium free of Y-27632 and the medium was replaced every day. In the meanwhile, cell morphology was observed by using an inverted microscope (OlympusCKX41, Japan) every day. If differentiated or abnormal clones were found, they were labeled and removed by suction with a negative-pressure suction apparatus (YX932D, China) in a biosafety cabinet. According to the size and the density of the clones, cells were digested with EDTA and passaged to a new PDA-CMC-VN modified 6-well plate every 3-5 days.

Quantitative RT-PCR Detection

RNA was extracted from cells with TRiZol, and was then subjected to reverse transcription PCR to synthesize cDNA, and finally the expression of Oct-4, Nanog, Sox-2, and Rex-1 was quantitatively detected. ACTB was used as a control gene, and primers for respective genes were listed in Table 1.

TABLE 1

Primer sequences for pluripotency detection genes

| Gene | Forward primer | Reverse primer |
|---|---|---|
| Oct-4 | CCTCACTTCACTGCACTGTA (SEQ ID NO: 4) | CAGGTTTTCTTTCCCTAGCT (SEQ ID NO: 9) |
| Nanog | TGAACCTCAGCTACAAACAG (SEQ ID NO: 5) | TGGTGGTAGGAAGAGTAAAG (SEQ ID NO: 10) |
| Sox-2 | CCCAGCAGACTTCACATGT (SEQ ID NO: 6) | CCTCCCATTTCCCTCGTTTT (SEQ ID NO: 11) |
| Rex-1 | TCGCTGAGCTGAAACAAATG (SEQ ID NO: 7) | CCCTTCTTGAAGGTTTACAC (SEQ ID NO: 12) |
| ACTB | CCCAGAGCAAGAGAGG (SEQ ID NO: 8) | GTCCAGACGCAGGATG (SEQ ID NO: 13) |

Immunofluorescent Detection

When human embryonic stem cells (H1, H9) and human induced pluripotent stem cell lines (hNF-C1 and UMC-C1) were continuously passaged to P20 on the PDA-CMC-VN surface, the expression of pluripotency markers Oct-4 and SSEA-3 was detected by immunofluorescence. The immunofluorescence experiment was performed in a 12-well plate, and the detailed steps of detection were introduced as follows.

1) The medium of human pluripotent stem cells was suctioned up, washed with DPBS once, and 1 ml of 4% paraformaldehyde was added for fixing at room temperature for 30 minutes.

2) The fixing liquid was suctioned, and washed with DPBS for 3 times, with gently shaking on a shaker for 2 min in each time.

3) 1 ml of 0.2% Triton-X100 (Sigma, Missouri, USA) was added and permeabilization was performed at room temperature for 30 min, and washed with DPBS for 3 times, with gently shaking on a shaker for 2 min in each time.

4) 1 ml of 3% BSA (Aladdin, Shanghai, China) was then used for solution blocking at room temperature for 2 hours.

5) An equal proportion mixture of 3% BSA and 0.2% Triton-X100 was used to formulate primary antibodies (Mouse Anti-Oct-3/4 IgG to Human (sc-5279); Mouse Anti-SSEA-3 IgM to Human (ab16286)) at 1:50, each well was added with 200 ul of the primary antibodies and was covered by a Parafilm wrap which was slightly smaller than the well, and the culture plate was placed into a needle box (wet box) containing water at 4° C. overnight.

6) The Parafilm wrap was picked off with a bended needle tip on the second day, the primary antibodies were suctioned, and washed with PBS for 3 times, with gently shaking on a shaker for 5 min in each time.

7) The following operations were performed under protection from light. Secondary antibodies (Goat Anti-Mouse Alexa Fluor 488 IgG (Molecular Probes, Invitrogen, USA) and Goat Anti-mouse Alexa Fluor 488 IgM (Molecular Probes, Invitrogen, USA)) were diluted with DPBS at a ratio of 1:500, and 400 ul of the secondary antibodies were added to each well and reaction was performed for 1 h.

8) Washed with DPBS for three times, with gently shaking on a shaker for 5 min in each time. DAPI was diluted with DPBS at a ratio of 1:5000, and 500 ul was added to each well, and staining was performed at room temperature for 5 min.

9) New DPBS was added after washing with DPBS once, a Nikon Eclipse E800 microscope or a Zeiss Axiovert 200M inverted confocal microscope was used for observation and to take photos. Excitation wavelengths of DAPI and green fluorescent labeled antibody were 405 nm and 488 nm, respectively.

Flow Cytometry Analysis

When 2 hESCs lines (H1, H9) and 2 hiPSCs lines (hNF-C1 and UMC-C1) were continuously passaged to P20 on the PDA-CMC-VN surface, positive expression percentages of their pluripotency markers Oct-4, SSEA-3, and Tra-1 60 were detected by flow cytometry. The detailed process of the experiment was as follows.

1) Cells to be treated were digested with 0.25% trypsin/EDTA (Stem Cell Technologies, Canada) in an incubator for 4 minutes, and a serum-containing medium was added to terminate the digestion and the cells were blown into single cells.

2) Centrifugation was performed at 200 g for 5 minutes, cells were resuspended with 1 ml of a flow cytometric buffer (DPBS, containing 2% FBS) and transferred to a 1.5 ml Eppendorf tube, and 200 ul of 1% paraformaldehyde was added for fixing at 37° C. for 5 minutes and centrifuging for 5 minutes.

3) Cells were resuspended with a flow cytometric buffer, 200 ul of 90% methanol pre-cooled on ice was added after centrifuging at 200 g, and permeabilization was performed on ice for 30 minutes. After centrifuging at 200 g for 5 minutes, washing was performed with a flow cytometric buffer twice.

4) An Oct-3/4 primary antibody (01550, StemCell Technologies, Canada) was diluted with a flow cytometric buffer at a ratio of 1:100. Cells were resuspended with 100 ul of the primary antibody solution, and incubated in an incubator for 30 min. After centrifuging at 200 g for 5 minutes, washing was performed with a flow cytometric buffer once. Steps 3-4 were suitable for the detection of the label Oct-4 in the cell, and were not required for cell surface markers SSEA-3 and Tra-1 60.

5) The following operations were performed under protection from light. An Oct-4 secondary antibody was diluted with a flow cytometric buffer at a ratio of 1:500, resuspended with a volume of 200 ul, and was incubated in an incubator for 30 min. In the meanwhile, directly labeled antibodies, SSEA-3 (60061PE, StemCell Technologies, Canada) and Tra-1 60 (60064PE, StemCell Technologies, Canada), were diluted with a flow cytometric buffer at a ratio of 1:100, and cells were resuspended with 100 ul of the solution and incubated in an incubator for 30 min. After the completion of incubation, centrifugation was performed at 200 g for 5 minutes.

6) After washing with a flow cytometric buffer once, cells were washed and resuspended with 600 ul of the flow cytometric buffer. After filtration, the expression of pluripotency factors was detected by BD FACS Calibur System (LSRFortessa, USA) and analyzed by software Flowjo.

4.4 Karyotype

After 5 human pluripotent stem cell lines were subjected to 20 passages of subculturing on a PDA-CMC-VN modified 6-well plate, they were back passaged to a 10 cm dish pre-plated with Matrigel to perform karyotype detection. After the cells grew to a density of 75%-85%, colchicine (Dahui Biotech, China) was added at a concentration of 50 $\mu g \cdot ml^{-1}$ and cells were treated in an incubator for 1 h. After rinsing with DPBS twice, cells were digested with 0.25% Trypsin/EDTA into single cells. After centrifuging at 200 g for 5 minutes, the supernatant was discarded. Cells were resuspended with 8 ml of a 0.075 mol/L KCl solution preheated at 37° C. and then placed in a water bath at 37° C. for reaction for 20 minutes. Thereafter, 2 ml of a newly formulated Carnoy's fixative (methanol:glacial acetic acid=3:1) was added and treatment continued for 10 minutes. After completion of cell fixation, centrifugation was performed at 200 g for 5 minutes, and cells were resuspended with a fixative subjected to an ice bath and slices were made. The arrangement of chromosomes was observed by using a BX51 microscope (Olympus, Japan).

Experiment on Formation of Embryoid Bodies

When growing to about 70% area of the culture plate, H1 hESCs and hNF-C1 hiPSCs, which were subjected to 20 passages of subculturing on PDA-CMC-VN, were digested with Dispase of 1 $mg \cdot mL^{-1}$ for 7 minutes. After washing with a DMEM/F12 medium for 3 times, an EB medium (a DMEM/F12 basal medium containing 20% bovine serum albumin, 2 mM L-glutaMax, 1% (wt/vol) NEAA, and 0.1 mM β-mercaptoethanol) was added, and cell clones were mechanically scraped off and transferred to a low-adhesion 6-well culture plate for suspension culture for 8 days. The medium was supplemented or the medium was replaced every 2-3 days according to the conditions of cells. Thereafter, embryoid bodies were transferred to PDA-CMC-VN for adherent culture for 8 days with the medium replaced every other day. Finally, cells were treated with Trizol and total RNA was extracted, and the expression of triploblastic marker genes was detected by fluorescence quantitative PCR (for primers, see Table 2) and was compared to that in undifferentiated human pluripotent stem cells.

drawn, sectioned, and stained with hematoxylin-eosin. Typical cells of three germ layers were sought for by microscopic observation.

Figure 4:
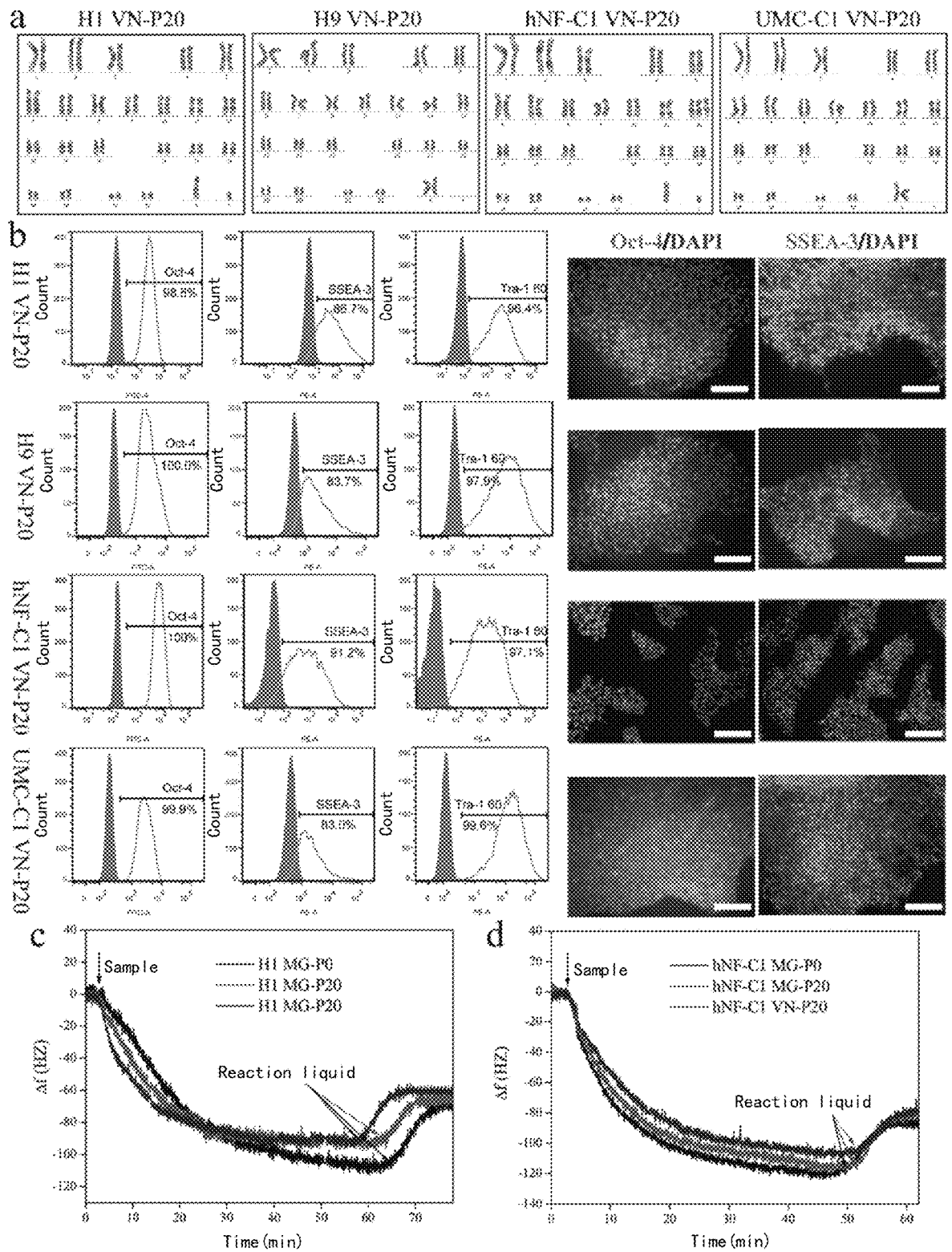
FIG. 4 shows that the PDA-CMC-VN surface supports long-term self-renewal of human pluripotent stem cells. (a) Karyotype analysis of 4 human pluripotent stem cell lines (H1 hESCs, H9 hESCs, hNF-C1 hiPSCs, and UMC-C1 hiPSCs) upon continuous passage to P20 on a PDA-CMC-VN surface. (b) The expression of pluripotency markers Oct-4, SSEA-3, and Tra-1 60 in 4 human pluripotent stem cell lines was detected by using flow cytometry (left panel) and immunofluorescence (right panel). (c) The telomerase activities of H1hESCs and hNF-C1hiPSCs on the material surface and the Matrigel surface after 20 passages of culturing were detected by using a quartz crystal microbalance.

Experimental Results 2 hESCs lines (H1 and H9) and 2 hiPSCs lines (hNF-C1 and UMC-C1) were selected and continuously passaged for more than 20 passages on the PDA-CMC-VN surface to judge whether this surface can support a long-term self-renewal of human pluripotent stem cells. When passaged to P20, all of 4 human pluripotent stem cell lines cultured on the PDA-CMC-VN surface maintained complete karyotypes (see FIG. 4a). The results of flow cytometry showed that, as for these 4 human pluripotent stem cell lines, positive expression percentages of cell pluripotency markers Oct-4, SSEA-3, and Tra-160 exceeded 99.4%, 82.6%, and 96.4%, respectively (see the left panel of FIG. 4b). It was further demonstrated by the immunofluorescence experiment that all of these cell clones highly expressed pluripotency markers Oct-4 and SSEA-3 (see the right panel of FIG. 4b).

By experiments of embryoid body formation and teratoma formation, we further confirmed that H1 hESCs and hNF-C1 hiPSCs still maintained pluripotency after more than 20 passages of culturing on the PDA-CMC-VN surface. H1

TABLE 2

Primer sequences for triploblastic identification of embryoid bodies

| Gene | Forward primer | Reverse primer |
| --- | --- | --- |
| AFP | ATTGGCAAAGCGAAGCTG (SEQ ID NO: 14) | GCTGTGGCTGCCATTTTT (SEQ ID NO: 23) |
| GATA4 | CAGAAAACGGAAGCCCAA (SEQ ID NO: 15) | TTGCTGGAGTTGCTGGAAG (SEQ ID NO: 24) |
| SOX17 | ACGGAATTTGAACAGTAT (SEQ ID NO: 16) | CAGGATAGTTGCAGTAAT (SEQ ID NO: 25) |
| MSX1 | TGCCTCGCTCTACGGTGCCT (SEQ ID NO: 17) | GGCTGGAGGAATCGGCTGGC (SEQ ID NO: 26) |
| CDH5 | GATCAAGTCAAGCGTGAGTCG (SEQ ID NO: 18) | AGCCTCTCAATGGCGAACAC (SEQ ID NO: 27) |
| T | GTGGGCCTGGAGGAGAGCGA (SEQ ID NO: 19) | TTGTCCGCCGCCACGAAGTC (SEQ ID NO: 28) |
| PAX6 | TTGCTTGGGAAATCCGAG (SEQ ID NO: 20) | TGCCCGTTCAACATCCTT (SEQ ID NO: 29) |
| SOX1 | TTTCCCCTCGCTTTCTCA (SEQ ID NO: 21) | TGCAGGCTGAATTCGGTT (SEQ ID NO: 30) |
| β-actin | CCCAGAGCAAGAGAGG (SEQ ID NO: 22) | GTCCAGACGCAGGATG (SEQ ID NO: 31) |

Detection of Teratoma Generation

Figure 5:
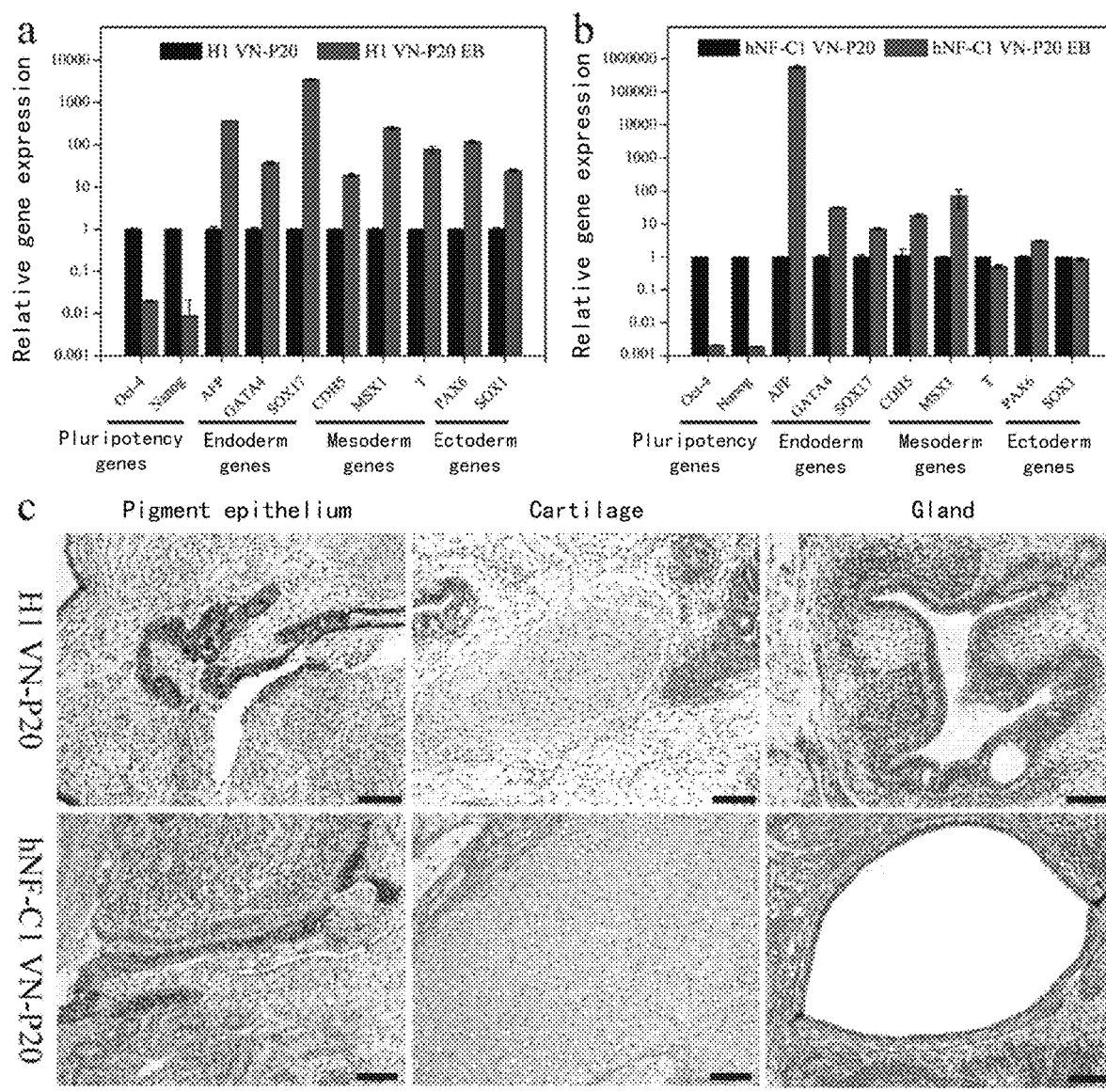
FIG. 5 confirms that H1 hESCs and hNF-C1 hiPSCs maintain multiple differentiation potential after continuous passage to P20 on the PDA-CMC-VN surface. (a-b) Whether the triploblastic marker genes were expressed by embryoid bodies formed by cells was analyzed by RT-PCR. (c) Cell samples were injected into a NOD/SCID mouse to form teratoma, which was sectioned and then stained with hematoxylin-eosin. Scale: 200 μm.

H1 hESCs and hNF-C1 hiPSCs, which had been subjected to 20 passages of subculturing on PDA-CMC-VN, were back passaged to Matrigel and cultured so as to be used in the experiment of teratoma generation. Cells to be injected were digested with Dispase, resuspended with 1:80 diluted Matrigel, and subcutaneously injected into NOD-SCID mice with a cell count of one million, and markers were made. When teratoma formed and grew to a diameter of 1 cm, the mouse was sacrificed. Typically, teratoma would generate after about 6-8 weeks. The teratoma was withhESCs and hNF-C1 hiPSCs, which were cultured on the PDA-CMC-VN surface, were suspended for 8 days and adherently cultured for 8 days, and the total RNA of the cells was extracted. It was demonstrated by the results of q-PCR that all of embryoid bodies formed by H1 hESCs and hNF-C1 hiPSCs on the PDA-CMC-VN surface expressed triploblastic genes (see FIGS. 5a-b). Furthermore, teratoma was formed within 6-8 weeks after these cells were subcutaneously injected into nude mice, and comprised tissues derived from three germ layers (see FIG. 5c). It was demonstrated by these results that H1 hESCs and hNF-C1 hiPSCs, which were cultured on the PDA-CMC-VN surface for a long-term, still maintained a multiple differentiation potential.

Example 5. PDA-CMC-VN Device Supported Directional Differentiation of Human Pluripotent Stem Cells into Nerve-Like Cells and Cardiac-Muscle-Like Cells When H9 hESCs were continuously passaged to the 15th passage on the PDA-CMC-VN surface, neural directional induction differentiation was performed by using a STEMdiff neural system (Stem Cell Technologies, Canada) according to the instructions of manufacturer. Furthermore, we performed a differentiation experiment of H9 hESCs into cardiac muscle cells according to the method reported in the reference (Yang, L. et al. Human cardiovascular progenitor cells develop from a KDR+ embryonic-stem-cell-derived population. Nature, 2008, 453, 524-528). The experimental method was same as that reported in the reference except that the media used on day 0, day 1, and day 4 were as shown below. Medium on day 0: Stempro-34 SFM10640 medium, Glutamin (100×), transferrin (0.15 mg/ml), 1-thioglycerol (6.5 ul/ml in 500 ml medium, 3 ul/ml of backbone), ascorbic acid (50 ug/ml), BMP4 (0.05 ng/ml), Y27632 (10 ug/ml). Medium on day 1: Stempro-34 SFM 10640 medium, Glutamin (100×), bFGF (6 ng/ml), Activin A (2.5 ng/ml), ascorbic acid (50 ug/ml), BMP4 (10 ng/ml). Medium on day 4: Stempro-34 SFM 10640 medium, Glutamin (100×), transferrin (0.15 mg/ml), 1-thioglycerol (6.5 ul/ml in 500 ml medium, 3 ul/ml of backbone), ascorbic acid (50 ug/ml), Y27632 (10 ug/ml), SB431542 (10 nM).

After nerve cells and cardiac muscle cells formed by directional differentiation were fixed with 4% paraformaldehyde, immunofluorescence staining was used to detect whether related markers were expressed so as to perform identification. Nerve-specific antibodies used were SOX-1 (R&D AF3369, USA), Nestin (R&D MAB1259, USA), MAP-2 (Millipore AB5622, USA), and Anti-β-Tubulin III (TUJ-1, Sigma-Aldrich T3952, USA); and cardiac-muscle-cell-specific antibodies were α-actinin (Abcam AB9465, United Kingdom) and β-myosin (R&D MAB4470, USA).

Experimental Results

Figure 6:
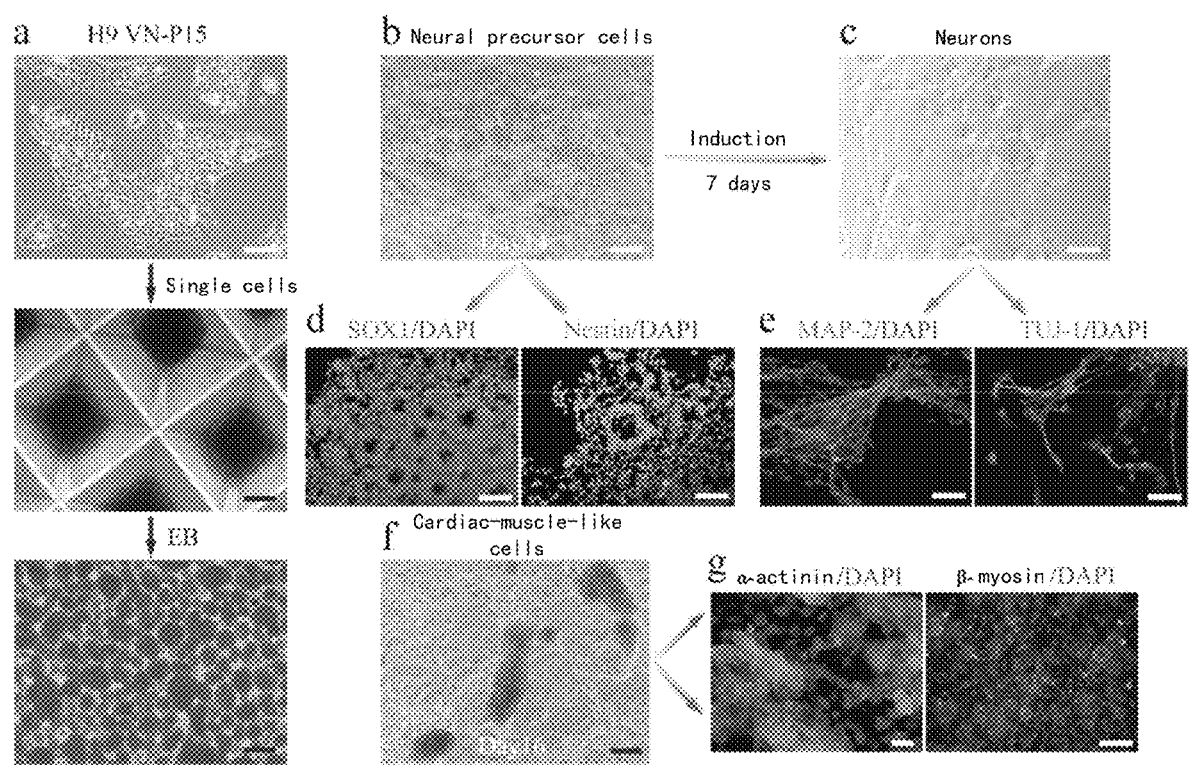
FIG. 6 shows the directional induction differentiation of H9 hESCs into nerve cells and cardiac muscle cells on the PDA-CMC-VN surface. (a) The 15th passage of H9 hESCs cultured on the PDA-CMC-VN surface (top panel) were digested into single cells, and then seeded onto an AggreWell™ 800 plate (middle panel) to form uniform embryoid bodies (bottom panel). (b) After H9 hESCs were induced in a neural induction culture medium for 14 days, a neural rosette was formed. (c) After these neural rosettes continued to be inducted for 7 days, neuron cells appeared. (d-e) Sox-1 (red)/Nestin (green) and MAP-2 (green)/TUJ-1 (green) were detected by immunofluorescence to identify neural precursor cells (d) and neuron cells (e) formed by induction, respectively. (f) Beating cardiac muscle cells were formed after H9 hESCs cultured on the PDA-CMC-VN surface were inducted for 16 days. (g) Cardiac muscle markers, α-actinin (green) and β-myosin (green). Cell nuclei were stained with DAPI (blue). White scale: 100 μm; Black scale: 200 μm.

The 15th passage of H9 hESCs cultured on the PDA-CMC-VN surface formed uniform embryoid bodies by using an AggreWell™ 800 plate (FIG. 6a), and differentiated into nerve cells and cardiac muscle cells in the case of defined components, respectively. After H9 hESCs were induced in a neural induction culture medium for 14 days, a neural rosettes was formed (FIG. 6b) and neural markers Sox-1 and Nestin were positively expressed (FIG. 6d), which demonstrated the successful induction into neural precursor cells. In the meanwhile, we picked up the neural rosette, which was cultured in a neural rosette selective medium for 7 days, and a typical neuron morphology appeared (FIG. 6c), and the immunofluorescence staining experiment demonstrated the positive expression of neuron markers MAP-2 and TUJ-1 (FIG. 6e), which demonstrated the successful differentiation into neuron cells. Furthermore, beating cardiac muscle cells were formed after embryoid bodies formed by H9 hESCs were induced on the PDA-CMC-VN surface for 16 days (FIG. 6f), and these cells expressed cardiac muscle markers, α-actinin and β-myosin. These experimental results illustrated that the PDA-CMC-VN surface supported a directional induction differentiation of hESCs into nerve cells and cardiac muscle cells in case of defined components.

Example 6. PDA-CMC-VN.BFP-1 Device Promoted a Directional Differentiation of Human Pluripotent Stem Cells into Osteoblasts Manufacture and Characterization of PDA-CMC-VN-.BFP-1 Device The manufacture of the PDA-CMC modified cell culture plate was as described above, and 5 mg of a VN peptide was dissolved in 3.1 ml PBS buffer in a super clean bench to obtain a concentration of 1 mM. 5 mg of a BFP-1 peptide was dissolved in 3.0 ml PBS buffer to obtain a 1 mM BFP-1 peptide solution. The prepared VN and BFP-1 peptide solutions were mixed at volume ratios of 10:0, 7:3, and 5:5 to obtain three groups of peptide mixed solutions, which were $VN_{10}/BFP-1_0$ (briefly referred to as VN), $VN_7/BFP-1_3$ (briefly referred to as 7:3), and $VN_5/BFP-1_5$ (briefly referred to as 5:5). A PDA-CMC-VN/BFP-1 peptide mixture-modified cell culture plate was then obtained by using the NHS/EDC activation method as described above.

Furthermore, we performed a quantitative study of peptide grafting on the surface-grafted VN and BFP-1 peptides by using a VN peptide labeled by fluorescin FITC (FITC-KGGPQVTRGDVFTMP (SEQ ID NO:1)) and a BFP-1 peptide labeled by rhodamine (Rho-KGGQGFSYPYKAVF-STQ (SEQ ID NO:32)). First, FITC-VN and Rho-BFP-1 peptide solutions having a concentration gradient of 0.2 mM, 0.4 mM, 0.6 mM, 0.8 mM, 1.0 mM, and 1.2 mM were formulated with a sterile PBS solution, respectively, and then 200 ul of peptide gradient solutions were added to a Corning 24-well plate, respectively (3 duplicate wells for each group). By using a full-wavelength microplate reader, the fluorescence value of the VN peptide was measured with excitation light of 488 nm and absorption light of 525 nm and the fluorescence value of the BFP-1 peptide was measured with excitation light of 532 nm and absorption light of 582 nm to establish a fluorescence-density standard curve. Thereafter, three groups of fluorescent peptide mixed solutions were formulated, which were $VN_{10}/BFP-1_0$ (briefly referred to as VN), $VN_7/BFP-1_3$ (briefly referred to as 7:3), and $VN_5/BFP-1_5$ (briefly referred to as 5:5). They were grafted onto an activated PS-PDA-CMC surface by using the method described above, and washed with pure water for 3 times, and fluorescence values were measured under the same conditions.

Directional Differentiation of Human Pluripotent Stem Cells into Osteoblasts

H9 hESCs (the passage number was 30-50 passages) and UMC-C1 hiPSCs (the passage number was 30-45 passages) cultured on the Matrigel surface were digested into single cells with an enzyme Acutase, and were then seeded onto material surfaces (VN group, 7:3 group, and 5:5 group). ROCK inhibitor (Y-27632) was added to MTESR™1 to promote the adhesion of single cells. Most of cells were completely adherent after 12 h, and the medium was replaced with an MTESR™1 medium free of ROCK inhibitor (Y-27632) at this time. After continuing to culture for 1 day, the MTESR™1 medium was replaced with an osteogenic induction medium (an α-MEM medium containing 10% FBS, 5 μg/ml vitamin C (AA), 10 mM β-sodium glycerophosphate (β-GP), and $10^{-8}$M dexamethasone), and the medium was freshened every 2 days until the 28th day. In the cell culture plate cultured to the 28th day, washing with cool PBS was performed for three times, and 4% paraformaldehyde was added for fixing for 30 min. 1 ml of an aqueous alizarin red solution having a mass fraction of 2% (pH=4.2) was added to each well and reaction was performed for 20 min, and the staining results of calcium nodules were photographed by an inverted light phase contrast microscope after washing with distilled water several times. Thereafter, 500 ul of a hexadecylpyridine solution having a mass fraction of 1% was added to each well. After complete reaction was performed, 100 ul of the supernatant was taken from each well and transferred to a new 96-well plate, and 3 duplicates were produced for each group. The absorbance was measured in a full-wavelength microplate reader using a wavelength of 490 nm so as to quantify the calcium nodules formed.

Experimental Results

Figure 7:
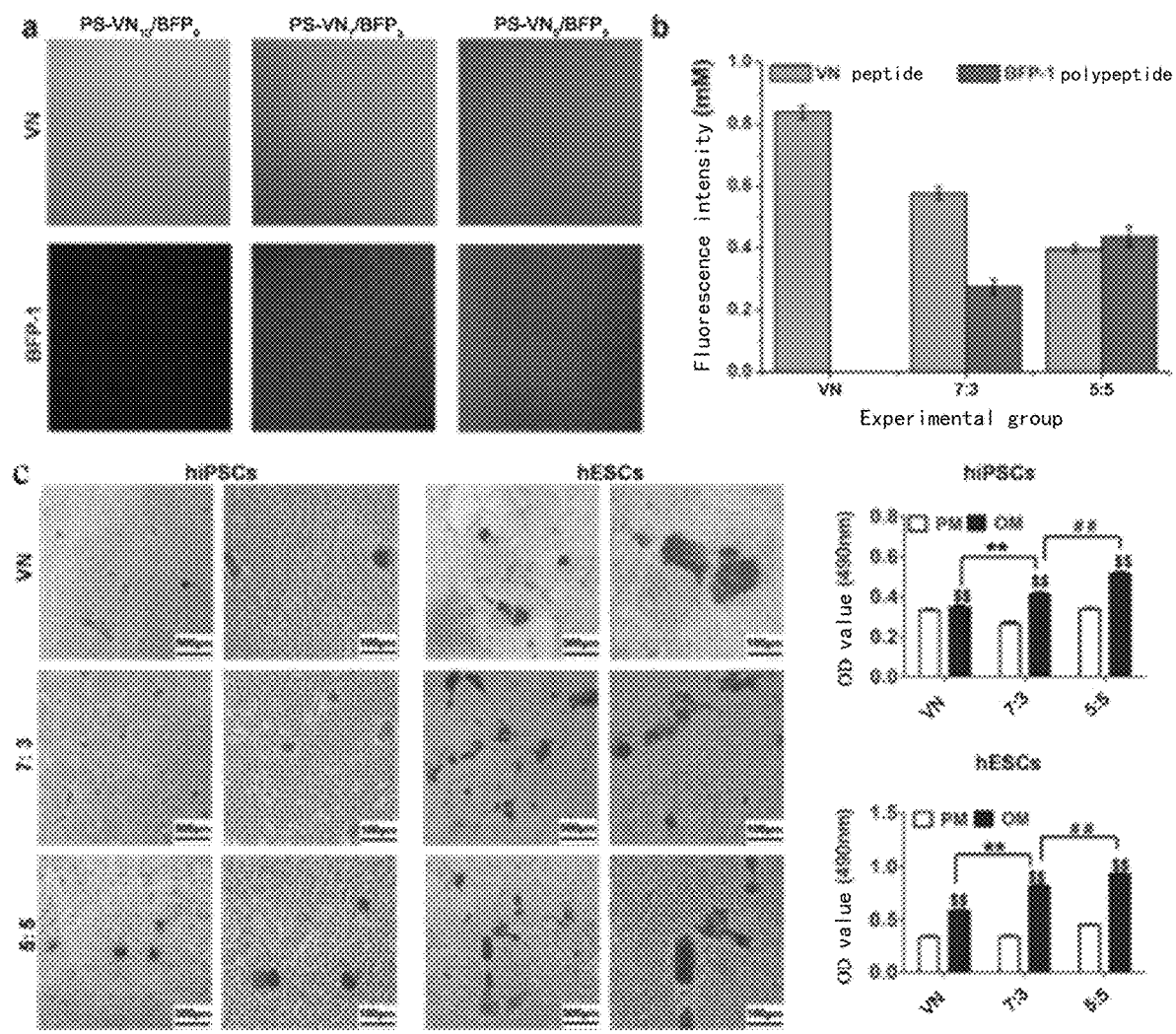
FIG. 7 shows the results of qualitative and quantitative characterizations of fluorescent peptides on PS-PDA-CMC-VN/BFP-1 peptide mixture-grafted material surfaces (a-b). Results of alizarin red qualitative staining and quantitative measurement of H9hESCs and UMC-C1 hiPSCs after 28 days of osteogenic induction on different PDA-CMC-VN/BFP-1 surfaces.

All of surfaces grafted with different peptide mixtures had relatively uniform fluorescence intensities, which demonstrated that we established relatively uniform material surfaces (FIG. 7a). The quantitative measurement results showed (FIG. 7b) that the green fluorescence intensity gradually decreased (representing that the grafted amount of the VN peptide gradually decreased) and the red fluorescence intensity gradually increased (representing that the grafted amount of the BFP-1 peptide gradually increased) from the VN group to the 7:3 group and to the 5:5 group. It was demonstrated that peptides were grafted onto material surfaces according to the preset ratios, and fluorescence quantitative experiments further demonstrated the proportion of grafted peptides.

FIG. 7c showed the results of alizarin red qualitative staining and quantitative measurement of respective groups after 28 days of osteogenic induction. Through 28 days of osteogenic induction, calcium nodules were formed on both H9 hESCs and UMC-C1 hiPSCs cultured on surfaces in the VN group, the 7:3 group, and the 5:5 group, and the quantity of calcium nodules formed gradually increased as the content of the BFP-1 osteogenic peptide increased. It was further demonstrated by the quantitative results that the osteogenic peptide indeed exerted a promoting effect on the osteogenesis of stem cells, but different cell lines behaved differently to some extent, in which H9 hESCs had a better osteogenic effect than that of UMC-C1 hiPSCs.

Example 7. PDA-CMC-VB Peptide Device Supported a Long-Term Self-Renewal of Human Pluripotent Stem Cells Examples 1-5 described above were repeated under the same experimental conditions except that the VN peptide in the PDA-CMC-VN device described above was replaced with the VB peptide designed and screened by our research team.

Figure 8:
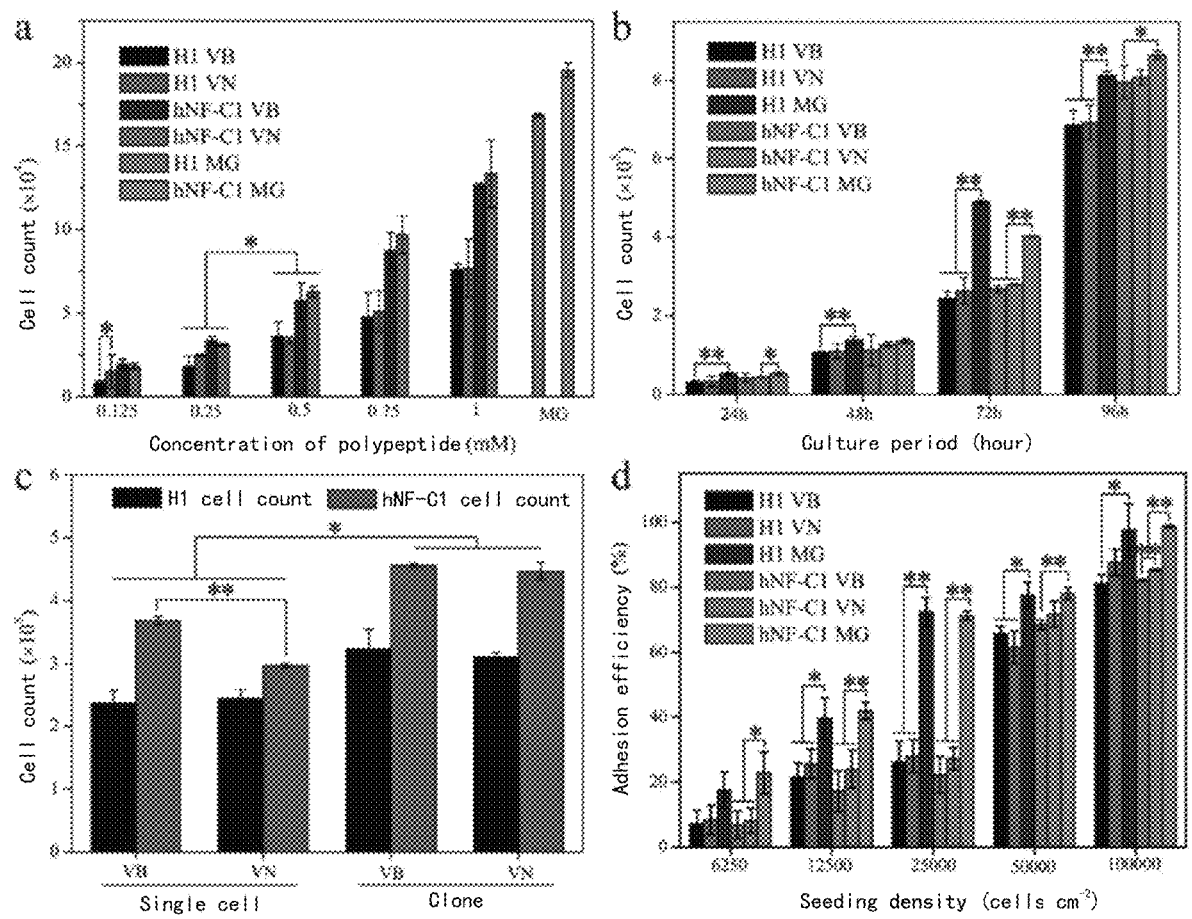
FIG. 8 shows that the VB peptide may substitute for VN peptide to be used in the culture of human pluripotent stem cells. (a) The effect of concentrations of peptides on the cell numbers of H1 hECSs and hNF-C1 hiPSCs cultured on the PDA-CMC-VB surface and the PDA-CMC-VN surface. (b) 96 h growth curves of H1 hECSs and hNF-C1 hiPSCs on the PDA-CMC-VB surface and the PDA-CMC-VN surface. (c) The cell numbers of H1 hECSs and hNF-C1 hiPSCs which were seeded as single cells or monoclones onto the PDA-CMC-VB surface and the PDA-CMC-VN surface and grown to the fourth day. (d) The cell numbers of H1 hECSs and hNF-C1 hiPSCs after 24 h adhesion on the PDA-CMC-VB surface and the PDA-CMC-VN surface in an inoculation density range of 6250-100000 cells cm2. Each of the above-described experiments utilized Matrigel as a control. * represents that p<0.05, and ** represents that p<0.01.

FIG. 8 showed that under conditions of EDTA digestion and the addition of ROCK inhibitor Y-27632, the PDA-CMC-VB surface and the PDA-CMC-VN surface had similar properties in terms of supporting the adhesion and the proliferation of H1 hECSs and hNF-C1 hiPSCs. First, the cell numbers of H1 hECSs and hNF-C1 hiPSCs, which were cultured on the PDA-CMC-VB surface and the PDA-CMC-VN surface for four days, were close to each other at all concentrations of the grafted peptides (0.25 mM, 0.5 mM, and 1 mM) except the concentration of 0.125 mM where the cell count of H1 hECSs cultured to the fourth day on VB was less than that on VN (p<0.05) (FIG. 8a). Furthermore, we also found that the cell count on the material surface on the fourth day also increased gradually as the concentration of peptides increased. It was demonstrated a relatively high concentration of peptide was necessary, and thus the concentrations of both VB and VN were 1 mM in subsequent experiments. Thereafter, it was demonstrated by 96 h growth curves that H1 hECSs and hNF-C1 hiPSCs on the PDA-CMC-VB surface and the PDA-CMC-VN surface had almost the same proliferation speed (FIG. 8b). In order to further compare the properties of VB and VN for promoting the adhesion of human pluripotent stem cells, we studied the effect of the digestion manner and the inoculation density of cells. FIG. 8c showed that the cell count of hNF-C1 hiPSCs which grew to the fourth day on the PDA-CMC-VB surface was significantly greater than that on the PDA-CMC-VN surface (p<0.01). It was demonstrated that the VB peptide was more suitable for single cell culture of hiPSCs than the VN peptide. There was no statistical difference between the cell numbers of H1 hECSs and hNF-C1 hiPSCs after 24 h adhesion on the PDA-CMC-VB surface and the PDA-CMC-VN surface within an inoculation density range of 6250-100000 cells·cm2 (FIG. 8d). These results demonstrated that the VB peptide designed and screened by us may substitute for VN peptide to be used in the culture of human pluripotent stem cells.

Figure 9:
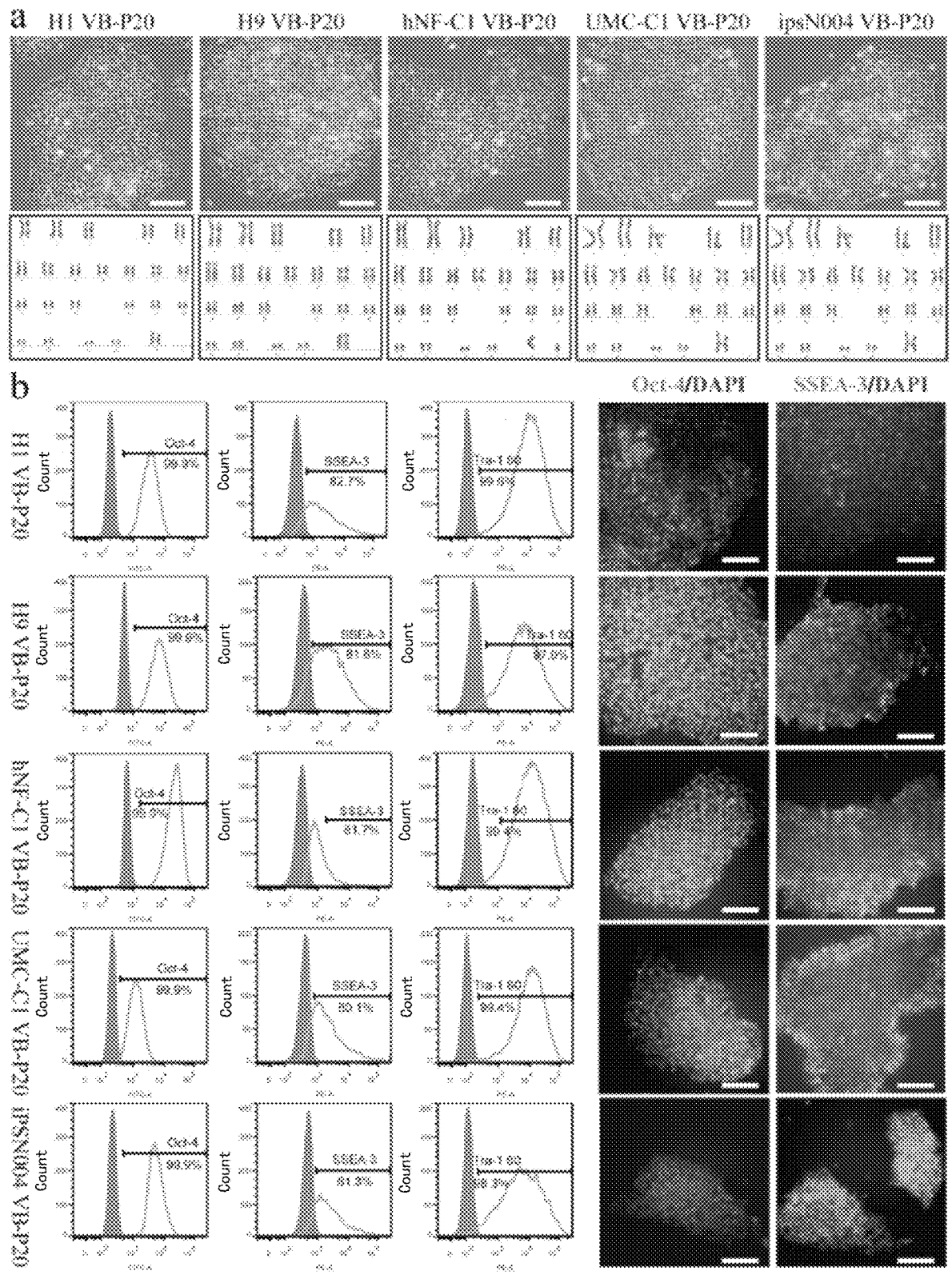
FIG. 9 shows that the PDA-CMC-VB surface supports long-term self-renewal of a plurality of human pluripotent stem cell lines. (a) Cell morphology and karyotype analysis of 5 human pluripotent stem cell lines (H1 hESCs, H9 hESCs, hNF-C1 hiPSCs, UMC-C1hiPSCs, and ipsN004 hiPSCs) upon continuous passage to P20 on the PDA-CMC-VB surface. (b) The expression of pluripotency markers Oct-4, SSEA-3, and Tra-1 60 in 5 human pluripotent stem cell lines was detected by using flow cytometry (left panel) and immunofluorescence (right panel). Scale: 100 μm.
Figure 10:
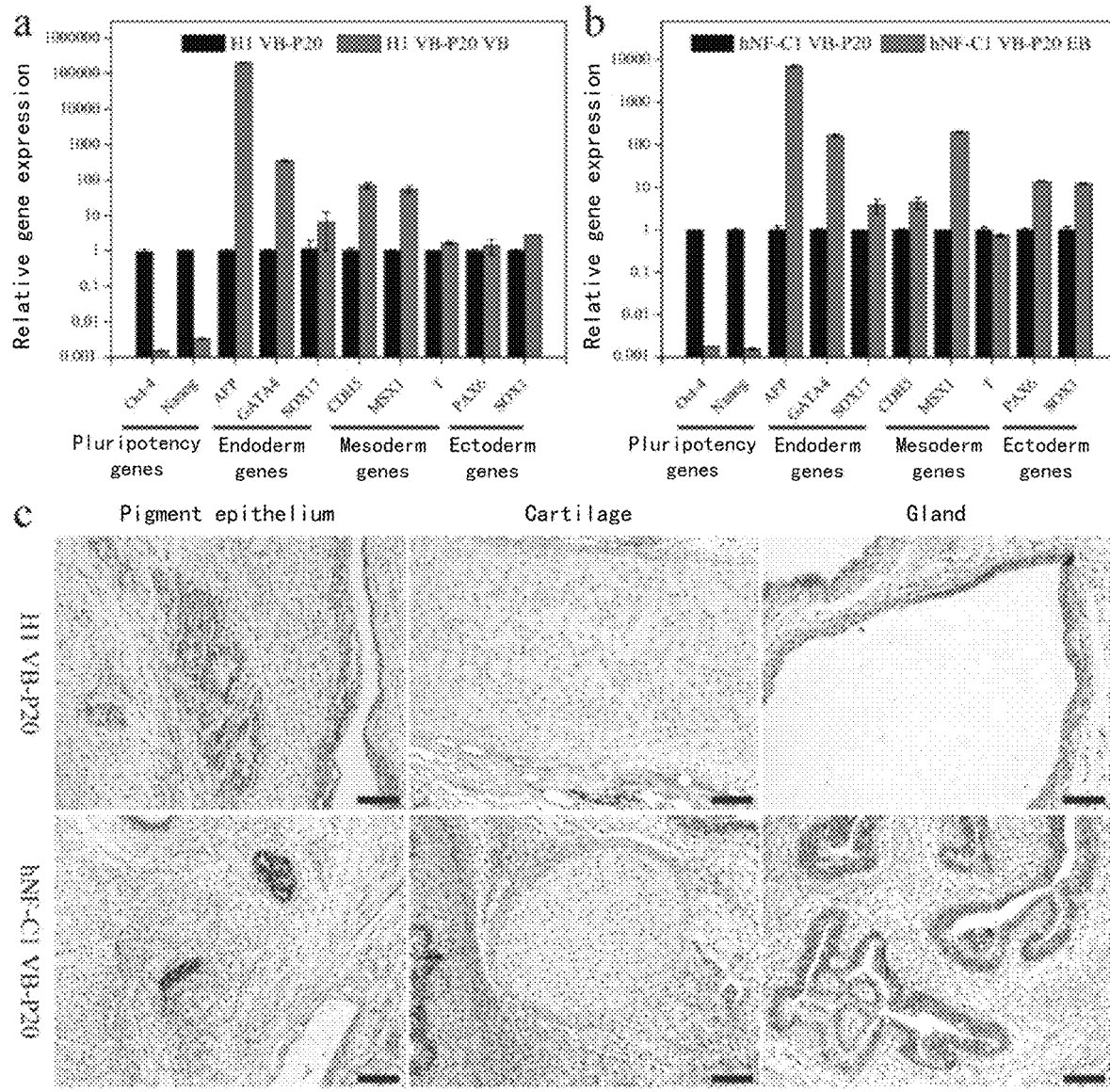
FIG. 10 confirms that H1 hESCs and hNF-C1 hiPSCs maintain multiple differentiation potential after continuous passage to P20 on the PDA-CMC-VB surface. (a-b) Whether the triploblastic marker genes were expressed by embryoid bodies formed by cells was analyzed by RT-PCR. (c) Cell samples were injected into a NOD/SCID mouse to form teratoma, which was sectioned and then stained with hematoxylin-eosin. Scale: 200 μm.
Figure 11:
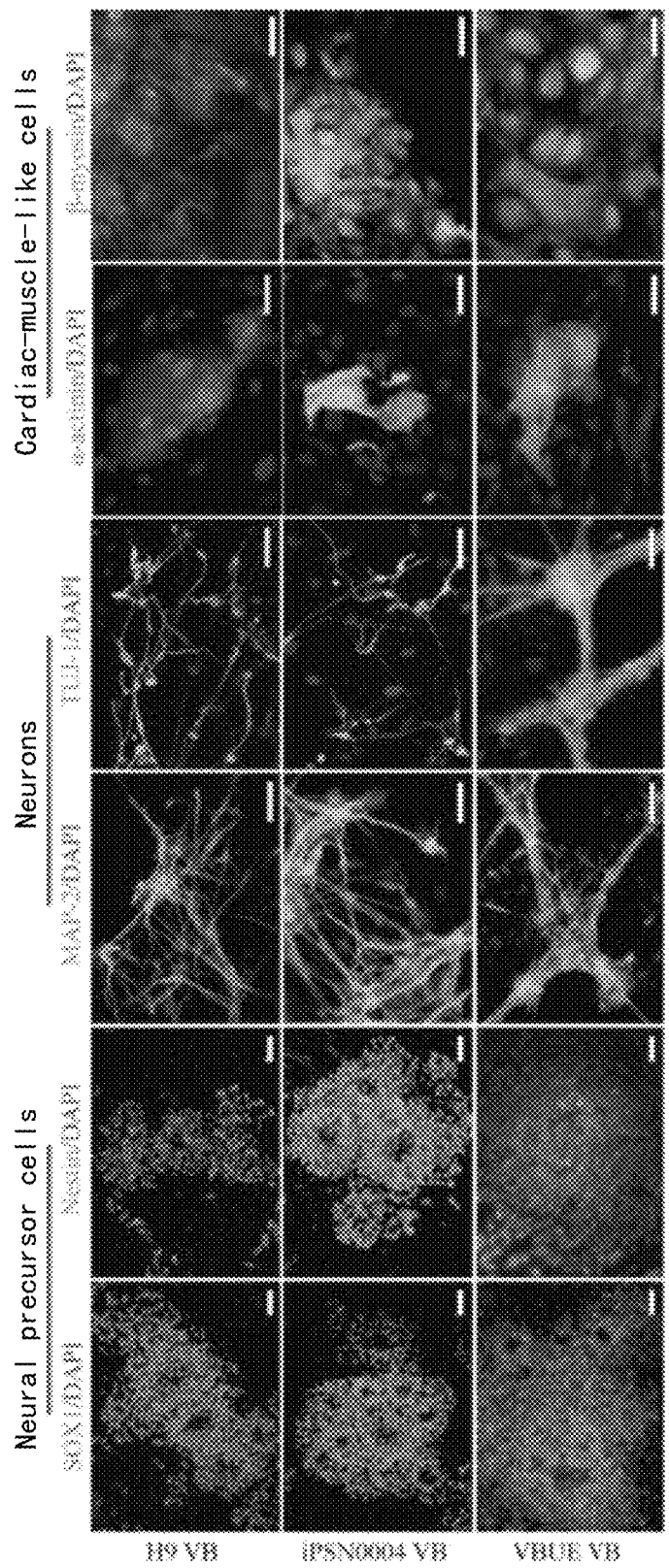
FIG. 11 shows that all of 3 human pluripotent stem cell lines, H9 hESCs, iPSN004 hiPSCs and VBUE hiPSCs, are capable of directionally differentiating into neural precursor cells, neuron cells, and cardiac muscle cells on the PDA-CMC-VB surface. Sox-1 (red)/Nestin (green), MAP-2 (green)/TUJ-1 (green), and α-actinin (green) and β-myosin (green) were detected by immunofluorescence to identify neural precursor cells, neuron cells, and cardiac muscle cells formed by induction, respectively. Cell nuclei were stained with DAPI (blue). Scale: 50 μm.

Thereafter, FIGS. 9 and 10 demonstrated that 5 human pluripotent stem cell lines (H1 hESCs, H9 hESCs, hNF-C1 hiPSCs, UMC-C1 hiPSCs, and ipsN004 hiPSCs) still maintained pluripotency after more than 20 passages of continuous passage on the PDA-CMC-VB surface. FIG. 11 showed that all of 3 human pluripotent stem cell lines, which were H9 hESCs, iPSN004 hiPSCs, and VBUE hiPSCs, were capable of directionally differentiating into nerve cells and cardiac muscle cells on the PDA-CMC-VB surface.

It shall be further emphasized that any technical feature or a combination of technical features described as a constituent for a certain technical solution in this specification may also be suitable for other technical solutions, in the case of being implementable and not obviously departing from the gist of the invention. Furthermore, technical features described as constituents for different technical solutions may also be combined arbitrarily to constitute other technical solutions, in the case of being implementable and not obviously departing from the gist of the invention. The invention further comprises technical solutions obtained by combination in the cases described above, and these technical solutions are equivalent to be described in this specification.

Although the invention is illustrated by specific embodiments and Examples above, it is to be understood by the person skilled in the art that those are not intended to limit the scope of the invention and the scope of the invention should be determined by the claims.

INDUSTRIAL APPLICABILITY

According to the invention, a device useful in cell culture or cell experiments in vitro can be provided.

What is claimed is:

1. A device, comprising:
   a substrate,
   a polydopamine layer chemically attached to the substrate,
   a carboxymethyl chitosan layer chemically attached to the polydopamine layer, and
   a peptide layer chemically attached to the carboxymethyl chitosan layer, the peptide layer comprising:
   (a) a peptide A, wherein peptide A is a peptide composed of the amino acid sequence of SEQ ID NO:1; and
   (b) a compound B having a function of promoting directional differentiation of human pluripotent stem cells, wherein compound B is a BFP-1 peptide composed of the amino acid sequence of SEQ ID NO: 32.

2. The device according to claim 1, wherein the distribution density of the peptide A in the peptide layer is 1-200 μg/cm$^2$.

3. The device according to claim 1, wherein the distribution density of the compound B in the peptide layer is 1-200 μg/cm$^2$.

4. A method for culturing cells in vitro, wherein the method is selected from the group consisting of:
   (1) culturing human somatic cells on the surface of the device of claim 1 and inducing the human somatic cells to be reprogrammed into human pluripotent stem cells; or
   (2) culturing human pluripotent stem cells adhered on the surface of the device of claim 1.

5. A method for promoting directional differentiation of human pluripotent stem cells in vitro using the device according to claim 1, comprising:
   step B: culturing human pluripotent stem cells on the surface of the device of claim 1 by using a directional induction medium.

6. The method according to claim 5, further comprising:
   step A: before the step B, culturing human pluripotent stem cells on the surface of the device of claim 1 by using a medium capable of maintaining self-renewal of human pluripotent stem cells.

7. The method according to claim 5, wherein the method is a method for promoting directional differentiation of human pluripotent stem cells into osteoblasts, and wherein the directional induction medium is an αMEM medium containing β3-mercaptoethanol, dexamethasone, vitamin C, and fetal bovine serum.

8. The method according to claim 5, wherein the method is a method for promoting directional differentiation of human pluripotent stem cells into neural precursor cells, and wherein the directional induction medium is an N2B27 culture broth supplemented with neural growth factors NGF and rmNoggin.

9. The method according to claim 5, wherein the method is a method for promoting directional differentiation of human pluripotent stem cells into cardiac muscle cells, which comprises culturing human pluripotent stem cells by using a MEF-CM medium containing bFGF for 2-3 days, replacing with a RPMI+B27 medium on the first day of induction, adding Activin A and culturing for 24 h, adding EMF 4 and bFGF on the second day of induction and maintaining for four days without replacing medium, and replacing with a RPMI+B27 medium containing 50 ng/ml VEGF165 and continuing to culture.

10. The method according to claim 5, wherein the method is a method for promoting directional differentiation of human pluripotent stem cells into dental epithelial cells, and wherein the directional induction medium is a DMEM/F12 medium containing N2, BMP-4, and RA.

11. The method according to claim 5, wherein the method is a method for promoting directional differentiation of human pluripotent stem cells into hepatocytes, which comprises culturing human pluripotent stem cells for 3 days by using a RPMI/B27 induction medium supplemented with Activin A, then culturing for 4 days by using a RPMI/B27 induction medium supplemented with BMP2 and FGF4, culturing for 3 days by using a RPMI/B27 induction medium supplemented with Activin A, culturing for 6 days by using a RPMI/B27 induction medium supplemented with HGF and KGF, and culturing for 8 days by using an induction medium, which is a hepatocyte culture medium supplemented with SingleQuots (EGF free) and Oncostatin-M.

* * * * *